(12) United States Patent
Zhang et al.

(10) Patent No.: US 11,136,399 B2
(45) Date of Patent: Oct. 5, 2021

(54) TYPE I INTERFERON RECEPTOR ANTIBODY AND USE THEREOF

(71) Applicant: INSTITUTE OF BIOPHYSICS, CHINESE ACADEMY OF SCIENCES, Beijing (CN)

(72) Inventors: Liguo Zhang, Beijing (CN); Lishan Su, Beijing (CN); Jingyun Li, Beijing (CN); Jianping Ma, Beijing (CN)

(73) Assignee: INSTITUTE OF BIOPHYSICS, CHINESE ACADEMY OF SCIENCES, Beijing (CN)

( * ) Notice: Subject to any disclaimer, the term of this patent is extended or adjusted under 35 U.S.C. 154(b) by 153 days.

(21) Appl. No.: 16/317,035

(22) PCT Filed: Jul. 14, 2016

(86) PCT No.: PCT/CN2016/090018
§ 371 (c)(1),
(2) Date: Jan. 11, 2019

(87) PCT Pub. No.: WO2018/010140
PCT Pub. Date: Jan. 18, 2018

(65) Prior Publication Data
US 2019/0389956 A1  Dec. 26, 2019

(51) Int. Cl.
C07K 16/28 (2006.01)
(52) U.S. Cl.
CPC ...... *C07K 16/2866* (2013.01); *C07K 2317/24* (2013.01); *C07K 2317/76* (2013.01)
(58) Field of Classification Search
None
See application file for complete search history.

(56) References Cited

U.S. PATENT DOCUMENTS

| | | | |
|---|---|---|---|
| 5,919,453 | A | 7/1999 | Benoit et al. |
| 6,713,609 | B1 | 3/2004 | Chuntharapai et al. |
| 7,179,465 | B2 | 2/2007 | Benoit et al. |
| 7,465,451 | B2 | 12/2008 | Benoit et al. |
| 7,662,381 | B2 | 2/2010 | Cardarelli et al. |
| 8,460,668 | B2 | 6/2013 | Cardarelli et al. |
| 8,828,393 | B2 | 9/2014 | Pickford et al. |
| 2006/0020118 | A1 | 1/2006 | Chuntharapai et al. |
| 2016/0376370 | A1 | 12/2016 | Cardarelli et al. |

FOREIGN PATENT DOCUMENTS

| | | |
|---|---|---|
| CN | 1795010 A | 6/2006 |
| EP | 1781705 B1 | 10/2014 |

OTHER PUBLICATIONS

Goldman, L.A. et al. "Characterization of Antihuman IFNAR-1 Monoclonal Antibodies: Epitope Localization and Functional Analysis", Journal of Interferon and Cytokine Research, vol. 19, No. 1, Jan. 31, 1999 (Jan. 31, 1999), pp. 15-26.
International Search Report and Written Opinion for PCT/CN2016/090018.
Matthew P. Hardy et al., "The soluble murine type I interferon receptor Ifnar-2 is present in serum, is independently regulated, and has both agonistic and antagonistic properties", Blood, Jan. 15, 2001, vol. 97, No. 2, pp. 473-482.
Elizabeth Cali Cutrone et al., "Identification of Critical Residues in Bovine IFNAR-1 Responsible for Interferon Binding", The Journal of Biological Chemistry, 2001, vol. 276, No. 20, pp. 17140-17148.
Gilles Uze et al., "Genetic Transfer of a Functional Human Interferon α Receptor into Mouse Cells: Cloning and Expression of Its cDNA", Cell, Jan. 26, 1990, vol. 60, pp. 225-234.
Daniela Novick et al., "The Human Interferon α/β Receptor: Characterization and Molecular Cloning", Cell, May 6, 1994, vol. 77, pp. 391-400.
Batya Cohen et al., "Ligand-Induced Association of the Type I Interferon Receptor Components", Molecular and Cellular Biology, Aug. 1995, vol. 15, No. 8, pp. 4208-4214.
T. Kim et al., "Serum levels of interferons in patients with systemic lupus erythematosus", Clin. exp. Immunol. (1987) 70, pp. 562-569.
Alan K. Foulis et al., "Immunoreactive α-Interferon in Insulin-Secreting β Cells in Type 1 Diabetes Mellitus", The Lancet, Dec. 19, 1987, pp. 1423-1427.
Masako Waguri et al., "Occurrence of IDDM during interferon therapy for chronic viral hepatitis", Diabetes Research and Clinical Practice, 23 (1994), pp. 33-36.
F. Monzani et al., "Thyroid autoimmunity and dysfunction associated with type I interferon therapy", Clin Exp Med (2004) 3, pp. 199-210.
Mark F. Prummel et al., "Interferon-α and Autoimmune Thyroid Disease", Thyroid, vol. 13, No. 6, 2003, pp. 547-551.
P.J. Hertzog et al., "Interferons in Rheumatoid Arthritis: Alterations in Production and Response Related to Disease Activity", Clinical Immunology and Immunopathology (1988), 48, pp. 192-201.
E. Destefano et al., "Acid-Labile Human Leukocyte Interferon in Homosexual Men with Kaposi's Sarcoma and Lymphadenopathy", The Journal of Infectious Diseases, Oct. 1982, vol. 146, No. 4, pp. 451-455.
Saroj Vadhan-Raj et al., "Immunological Variables as Predictors of Prognosis in Patients with Kaposi's Sarcoma and the Acquired Immunodeficiency Syndrome", Cancer Research, Jan. 1986, vol. 46, pp. 417-425.
Michael G. Tovey et al., "Role of the type I interferons in allograft rejection", Journal of Leukocyte Biology, Apr. 1996, vol. 59, pp. 512-517.

(Continued)

*Primary Examiner* — Gary B Nickol
*Assistant Examiner* — Jegatheesan Seharaseyon
(74) *Attorney, Agent, or Firm* — Jun He Law Offices P.C.; Zhaohui Wang

(57) ABSTRACT

The present disclosure discloses monoclonal antibodies binding to type I interferon alpha receptor and their uses. The antibodies are capable of inhibiting the biological activity of type I interferons, and can be used for treating, preventing, or diagnosing the diseases mediated by the type I interferons. Also provided are immunoconjugate, bispecific molecule and pharmaceutical compositions comprising the antibodies of the present disclosure.

21 Claims, 8 Drawing Sheets

Specification includes a Sequence Listing.

(56) References Cited

OTHER PUBLICATIONS

Eric Benizri et al., "Prolonged Allograft Survival in Cynomolgus Monkeys Treated with a Monoclonal Antibody to the Human Type I Interferon Receptor and Low Doses of Cyclosporine", Journal of Interferon and Cytokine Research (1998) 18, pp. 273-284.
Munther Khamashta et al., "Sifalimumab, an anti-interferon-α monoclonal antibody, in moderate to severe systemic lupus erythematosus: a randomised, double-blind, placebo-controlled study", Clinical and epidemiological research, Mar. 23, 2016, 75: 1909-1916.
Richard Furie et al., "Anifrolumab, an Anti-Interferon-a Receptor Monoclonal Antibody, in Moderate-to-Severe Systemic Lupus Erythematosus", Arthritis & Rheumatology, vol. 69, No. 2, Feb. 2017, pp. 376-386.
E.F. Morand et al., "Trial of Anifrolumab in Active Systemic Lupus Erythematosus", The New England Journal of Medicine, Jan. 16, 2020, vol. 382, No. 3, 211-221.
Brett S. Marro et al., "Progression of type 1 diabetes from the prediabetic stage is controlled by interferon-α signaling", PNAS, Apr. 4, 2017, vol. 114, No. 14, 3708-3713.
Angela Lombardi et al., "Interferon alpha: The key trigger of type 1 diabetes", Journal of Autoimmunity 94 (2018), 7-15.
N.-P. Andreou et al., "Inflammatory bowel disease pathobiology: the role of the interferon signature", Annals of Gastroenterology (2020) 33, 125-133.
Jun-Yi Li et al., "IRF/Type I IFN signaling serves as a valuable therapeutic target in the pathogenesis of inflammatory bowel disease", International Immunopharmacology 92 (2021) 107350, pp. 1-6.
Lawrence D. Jacobs et al., "Intramuscular Interferon Beta-Ia for Disease Progression in Relapsing Multiple Sclerosis", Annals of Neuroloby, vol. 39, No. 3, Mar. 1996, 285-294.
Stefanie Scheu et al., "Interferon β-Mediated Protective Functions of Microglia in Central Nervous System Autoimmunity", Int. J. Mol. Sci. 2019, 20, 190; 1-23.
Yihong Yao et al., "Type I Interferon: Potential Therapeutic Target for Psoriasis?", PLoS ONE, Jul. 2008, vol. 3, Issue 7, e2737, 1-14.
Ling-juan Zhang, "Type1 Interferons Potential Initiating Factors Linking Skin Wounds With Psoriasis Pathogenesis", Frontiers in Immunology, Jun. 2019, vol. 10, Article 1440, 1-8.
C. Carella et al. "Interferon-a-Related Thyroid Disease: Pathophysiological, Epidemiological, and Clinical Aspects", J Clin Endocrinol Metab, Aug. 2004, 89(8): 3656-3661.
Jamie C. Mandac et al., "The Clinical and Physiological Spectrum of Interferon-Alpha Induced Thyroiditis: Toward a New Classification", Hepatology, Apr. 2006, 661-672.
Bruno Cacopardo et al., "Rheumatoid arthritis following PEG-interferonalfa-2a plus ribavirin treatment for chronic hepatitis C: a case report and review of the literature", BMC Research Notes, 2013, 6:437, 1-4.
Theresa L. Wampler Muskardin et al., "Type I interferon in rheumatic diseases", Nat Rev Rheumatol. Mar. 21, 2018; 14(4): 214-228.
Anna-Marie Fairhurst et al., "Type I Interferons Produced by Resident Renal Cells May Promote End-Organ Disease in Autoantibody-Mediated Glomerulonephritis", J Immunol. Nov. 15, 2009; 183(10): 6831-6838.
Iacopo Gianassi et al., "Broad spectrum of interferon-related nephropathiesglomerulonephritis, systemic lupus erythematosus-like syndrome and thrombotic microangiopathy: A case report and review of literature", World J Nephrol Nov. 12, 2019; 8(7): 109-117.
Liang Cheng et al., "Blocking type I interferon signaling enhances T cell recovery and reduces HIV-1 reservoirs", The Journal of Clinical Investigation, Jan. 2017, vol. 127, No. 1, 269-279.
Liang Cheng et al., "Type I interferons suppress viral replication but contribute to T cell depletion and dysfunction during chronic HIV-1 infection", JCI Insight, Jun. 15, 2017, 1-13.

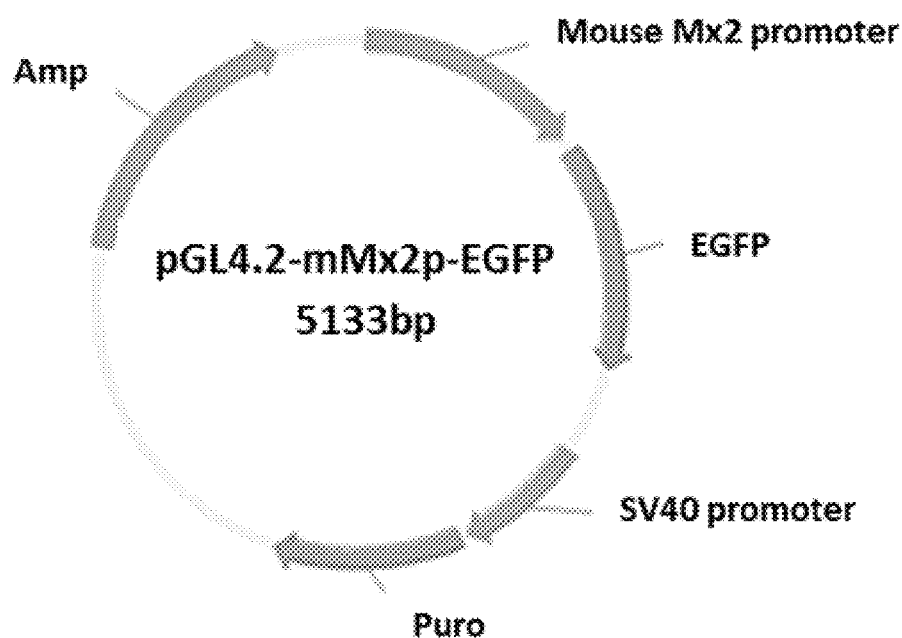
A
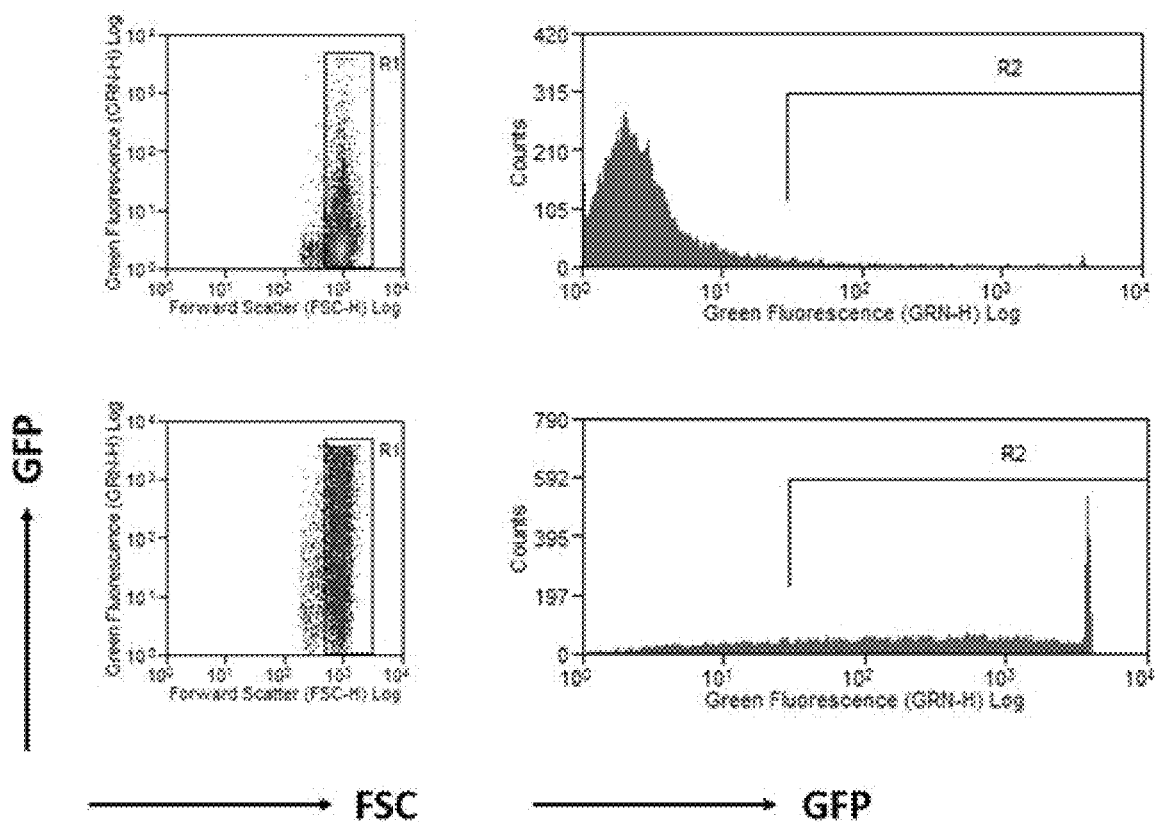
B
Figure 1

Signal peptide

M A W V W T L L F L M A A A Q S A Q A Q
1 ATG GCT TGG GTG TGG ACC TTG CTA TTC CTG ATG GCA GCT GCC CAA AGT GCC CAA GCA CAG

I Q L V Q S G P E L K K P G E T V K I S
61 ATC CAG TTG GTG CAG TCT GGA CCT GAG CTG AAG AAG CCT GGA GAG ACA GTC AAG ATC TCC

CDR1

C K A S G Y T F T N Y G M N W V K Q A P
121 TGC AAG GCT TCT GGG TAT ACC TTC ACA AAC TAT GGA ATG AAC TGG GTG AAG CAG GCT CCA

CDR2

G K G L K W M G W I N T Y T G E P T Y S
181 GGA AAG GGT TTA AAG TGG ATG GGC TGG ATA AAC ACC TAC ACT GGA GAA CCA ACA TAT TCT

D D F K G R F A F S L E T S A S T A N L
241 GAT GAC TTC AAG GGA CGG TTT GCC TTC TCT TTG GAG ACC TCT GCC AGC ACT GCC AAT TTG

Q I N N L K D E D A A T Y F C A R E G A
301 CAG ATC AAC AAC CTC AAA GAT GAG GAC GCG GCT ACA TAC TTC TGT GCA AGA GAG GGG GCT

CDR3

I Y Y G D Y V Y F G V W G A G T T V T V
361 ATC TAC TAT GGT GAC TAC GTG TAC TTC GGT GTC TGG GGC GCA GGG ACC ACG GTC ACC GTC

S S
421 TCC TCA

Figure 3

Signal peptide

M G F K M E S H T Q A F V F A F L W L S
1 ATG GGC TTC AAG ATG GAG TCT CAT ACT CAG GCC TTT GTA TTC GCG TTT CTC TGG TTG TCT

G V D G D I V M T Q S Q K F M S T S V G
61 GGT GTT GAT GGA GAC ATT GTG ATG ACC CAG TCT CAA AAA TTC ATG TCC ACA TCA GTA GGA

CDR1

D R V S I T C K A S Q N V G T A V A W Y
121 GAC AGG GTC AGC ATC ACC TGC AAG GCC AGT CAG AAT GTG GGT ACT GCT GTA GCC TGG TAT

CDR2

Q E K P G Q S P K L L I Y S A S N R Y T
181 CAA GAG AAA CCA GGA CAA TCT CCT AAA CTA CTG ATT TAC TCG GCA TCC AAT CGA TAC ACT

G V P D R F T G S G S G T A F T L T I S
241 GGA GTC CCT GAT CGC TTC ACA GGC AGT GGA TCT GGG ACA GCT TTC ACT CTC ACC ATC AGC

CDR3

N M Q S E D L A D Y F C Q Q Y Y N Y P L
301 AAT ATG CAG TCT GAA GAC CTG GCA GAT TAT TTC TGC CAG CAA TAT TAC AAT TAT CCT CTC

T F G A G T K L E V K R
361 ACG TTC GGT GCT GGG ACC AAG CTG GAG GTG AAA CGG

Figure 4

```
                    ┌─────────────────┐
                    │ Signal peptide  │
    M   A   W   V   W   T   L   L   F   L   M   A   A   A   Q   S   A   Q   A    Q
  1 ATG GCT TGG GTG TGG ACC TTG CTA TTC CTG ATG GCA GCT GCC CAA AGT GCC CAA GCA  CAG I   Q   L   V   Q   S   G   P   E   L   K   K   P   G   E   T   V   K   I   S
 61 ATC CAG TTG GTG CAG TCT GGA CCT GAG CTG AAG AAG CCT GGA GAG ACA GTC AAG ATC TCC
                                      ┌─────── CDR1 ────────┐
    C   K   A   S   G   Y   T   F   T   N   Y   G   V   N   W   M   K   Q   A   P
121 TGC AAG GCT TCT GGA TAT ACC TTC ACA AAC TAT GGA GTG AAC TGG ATG AAG CAG GCT CCA
                                                      ┌──── CDR2 ────┐
    G   K   G   L   K   W   M   G   W   I   N   T   Y   T   G   E   P   T   Y   A
181 GGA AAG GGT TTA AAG TGG ATG GGC TGG ATA AAC ACC TAC ACT GGA GAG CCA ACA TAT GCT D   D   F   K   G   R   F   A   F   S   L   E   T   S   A   S   T   A   Y   L
241 GAT GAC TTC AAG GGA CGC TTT GCC TTC TCT TTG GAA ACC TCT GCC AGC ACT GCC TAT TTA Q   I   N   N   L   K   N   E   D   T   A   T   Y   F   C   A   R   E   G   V
301 CAG ATC AAC AAC CTC AAA AAT GAG GAC ACG GCT ACA TAT TTC TGT GCA AGA GAG GGG GTT
                            ┌──── CDR3 ────┐
    Y   Y   Y   G   D   W   A   W   L   A   Y   W   G   Q   G   T   L   V   T   V
361 TAT TAC TAC GGT GAT TGG GCC TGG CTT GCT TAC TGG GGC CAA GGG ACC CTG GTC ACT GTC

S   A
421 TCT GCA
```

Figure 7

```
                    ┌─────────────────┐
                    │ Signal peptide  │
    M   E   S   Q   T   Q   V   F   V   Y   M   L   L   W   L   S   G   V   D   G
  1 ATG GAG TCA CAG ACT CAG GTC TTT GTA TAC ATG TTG CTG TGG TTG TCT GGT GTT GAT GGA D   I   V   M   T   Q   S   Q   K   F   I   S   T   S   V   G   D   R   V   S
 61 GAC ATT GTG ATG ACC CAG TCT CAA AAA TTC ATT TCC ACA TCA GTA GGA GAC AGG GTC AGC
                                      ┌──── CDR1 ────┐
    V   T   C   K   A   S   Q   N   V   G   T   N   V   A   W   Y   Q   Q   K   P
121 GTC ACC TGC AAG GCC AGT CAG AAT GTG GGT ACT AAT GTA GCC TGG TAT CAA CAG AAA CCA
                                      ┌── CDR2 ──┐
    G   Q   S   P   K   I   L   I   Y   S   T   S   Y   R   Y   N   G   V   P   D
181 GGT CAA TCT CCT AAA ACA CTG ATT TAC TCG ACA TCC TAC CGG TAC AAT GGA GTC CCT GAT R   F   T   G   S   G   S   G   T   D   F   T   L   T   I   S   N   V   Q   S
241 CGC TTC ACA GGC AGT GGA TCT GGG ACA GAT TTC ACT CTC ACC ATC AGC AAT GTG CAG TCT
                                              ┌──── CDR3 ────┐
    E   D   L   A   E   Y   F   C   Q   Q   Y   N   S   Y   Y   T   F   G   G   G
301 GAA GAC TTG GCA GAG TAT TTC TGT CAG CAA TAT AAC AGC TAT TAC ACG TTC GGA GGG GGG

T   K   L   E   I   K   R
361 ACC AAG CTG GAA ATA AAA CGG
```

Figure 8

TYPE I INTERFERON RECEPTOR ANTIBODY AND USE THEREOF

SEQUENCE LISTING

A copy of the Sequence Listing is submitted with the specification electronically via EFS-Web as an ASCII formatted sequence listing with a file name of "seq_20190814_ST25.txt", a creation date of Aug. 14, 2019, and a size of about 23 Kb. The sequence listing contained this ASCII formatted document is part of the specification and is herein incorporated by reference in its entirety.

FIELD OF THE INVENTION

The invention belongs to the field of biotechnology, and in particular relates to interferon alpha receptor I antibodies and their uses.

BACKGROUND OF THE INVENTION

Type I interferons (IFN-I) are a family of structurally related cytokines having antiviral, antitumor and immunomodulatory effects (Hardy et al. (2001) Blood 97: 473; Cutrone and Langer (2001) J. Biol. Chem: 276:17140). The IFN-I family consists of 5 members, including IFN-α (which includes 13 subtypes), IFN-β, IFN-ε, IFN-κ and IFN-ω. Interferon is a potent antiviral agent, but in some acute virus disease, excess human IFN-α cause symptoms of upper respiratory tract infection. Moreover, human IFN-α is associated with chronic viral infections in experimental animals and patients with chronic viral diseases such as pathogenesis of measles virus infection. Human IFN-α is a potent immunoregulatory molecule, which has the function of stimulating B cell activation, enhancing the cytotoxicity of NK cells, inhibiting T cell functions, regulating the expression of the major histocompatibility complex (MHC) I antigen expression. Furthermore, abnormal expression of type I interferons has been described in numerous autoimmune diseases, including systemic lupus erythematosus (SLE), type I diabetes, psoriasis, rheumatoid arthritis, multiple sclerosis, acquired immune deficiency syndrome (AIDS) and severe combined immunodeficiency disease.

All human type I interferons bind to a cell surface receptor (IFN alpha receptor, IFNAR) which is a heterodimer consisting of two transmembrane proteins, IFNAR-1 and IFNAR-2 (Uze et. al. (1990) Cell 60:225; Novick et al. (1994) Cell 77:391). Human IFNAR1 which belongs to the type II spiral-type cytokine receptors is an important component of IFN-I signaling pathway. It includes an extracellular domain that is composed of 4 type III fibronectin domains, a transmembrane domain and an intracellular domains composing of 100 amino acids. The four subdomains (SD) of IFNAR1 fold into domain 1 (SD1+SD2) and domain 2 (SD3+SD4). IFNAR1, IFNAR2 and IFN-I ligands form ternary signal complexes (Cohen B et. al. (1995) Mol Cell Biol 15(8): 4208-14), which is the first step of activation of signal transduction pathways. Therefore, targeting this receptor or blocking its downstream kinase activation has potential to blocking downstream biological effects of IFN-I related diseases.

U.S. Pat. No. 7,179,465 (2007) and U.S. Pat. No. 7,465,451 (2008) disclose an interferon alpha receptor 1 monoclonal antibody 64G12 that recognizes the extracellular domain SD1 of IFNAR1 and it has a neutralizing capacity against the biological properties of human type I interferons. U.S. Pat. No. 7,465,451 (2008) also discloses the uses of interferon alpha receptor 1 monoclonal antibody for treating or preventing IFN-I related disease, and the pharmaceutical uses of treating graft versus host disease (GVHD), autoimmune diseases such as systemic lupus erythematosus (SLE), type I diabetes, psoriasis, rheumatoid arthritis, multiple sclerosis, acquired immune deficiency syndrome (AIDS) and severe combined immunodeficiency disease, also acute virus infection diseases (e.g. upper respiratory infection) and chronic virus infection (e.g. Mumps Virus Infections). U.S. Pat. No. 6,713,609 (2004) discloses IFNAR1 monoclonal antibodies 2E1 and 4A7 that are capable of inhibiting the biological activity of multiple type I interferon, where 2E1 binds to the extracellular domain SD1 of IFNAR1, and 4A7 binds to the extracellular domain SD1 and SD2 of IFNAR1. U.S. Pat. No. 7,662,381 (2010) and U.S. Pat. No. 8,460,668 (2013) disclose an IFNAR1 monoclonal antibody 9D4 that binds to IFNAR1 and is capable of inhibiting the biological activity of type I interferons. The antibody binds to the extracellular domain SD3 of IFNAR1.

DESCRIPTION OF THE INVENTION

The first objective of the disclosure is to provide an anti-IFNAR1 monoclonal antibody.

The anti-IFNAR1 monoclonal antibodies provided herein bind to all or part of SD2 domain and/or all or part of SD3 domain, and inhibit the biological activity of type I interferons.

With respect to the above monoclonal antibodies, the antibodies or antigen-binding portions thereof exhibit one or more of the following properties:
  A) binding to IFNAR1;
  B) binding to all or part of SD2 domain and/or all or part of SD3 domain;
  C) inhibiting the biological activity of type I interferons;
  D) inhibiting the biological activity of type I interferons in type I interferon signaling reporter cells; and
  E) inhibiting the biological activity of type I interferons in agonist stimulated human peripheral blood mononuclear cells.

With respect to the above monoclonal antibodies, the antibodies or antigen-binding portions thereof comprise a heavy chain variable region encoded by a gene which is 1) or 2) as follows:
  1) the product of or derived from mouse IGHV9-3, IGHD2-13 and IGHJ1 genes;
  2) the product of or derived from mouse IGHV9-3, IGHD1-1 and IGHJ3 genes;
  the antibodies or antigen-binding portions thereof comprise a light chain variable region encoded by a gene which is 3) or 4) as follows:
  3) the product of or derived from mouse IGKV6-13 and IGKJ5 genes;
  4) the product of or derived from mouse IGHV6-15 and IGKJ2 genes.

With respect to the above monoclonal antibodies, the antibodies or antigen-binding portions thereof comprise a heavy chain variable region which is 5) or 6) as follows:
  5) the protein or peptide encoded by full length or part of mouse IGHV9-3 gene, the protein or peptide encoded by full length or part of mouse IGHD2-13 gene, the protein or peptide encoded by full length or part of mouse IGHJ1 gene;
  6) the protein or peptide encoded by full length or part of mouse IGHV9-3 gene, the protein or peptide encoded by full length or part of mouse IGHD1-1 gene, the protein or peptide encoded by full length or part of mouse IGHJ3 gene.

the antibodies or antigen-binding portions thereof comprise a heavy chain variable region which is 7) or 8) as follows:

7) the protein or peptide encoded by full length or part of mouse IGHV6-13 gene, the protein or peptide encoded by full length or part of mouse IGHJ5 gene.

8) the protein or peptide encoded by full length or part of mouse IGHV6-15 gene, the protein or peptide encoded by full length or part of mouse IGHJ2 gene.

With respect to the above monoclonal antibodies, the antibodies or antigen-binding portions thereof comprise:

a heavy chain variable region comprising sequentially the protein encoded by mouse IGHV9-3 gene, the protein encoded by mouse IGHD2-13 gene, and the protein encoded by mouse IGHJ1 gene; and a light chain variable region comprising the protein encoded by mouse IGHV6-13 gene, and the protein encoded by mouse IGHJ5 gene; or a heavy chain variable region comprising sequentially the protein encoded by mouse IGHV9-3 gene, the protein encoded by mouse IGHD1-1 gene, and the protein encoded by mouse IGHJ3 gene, and a light chain variable region comprising the protein encoded by mouse IGHV6-15 gene, and the protein encoded by mouse IGHJ2 gene.

With respect to the above monoclonal antibodies, the antibodies or antigen-binding portions thereof comprise a heavy chain variable region comprising a heavy chain variable region CDR1, a heavy chain variable region CDR2 and a heavy chain variable region CDR3;

a light chain variable region comprising a light chain variable region CDR1, a light chain variable region CDR2 and a light chain variable region CDR3;

wherein the amino acid sequence of the heavy chain variable region CDR1 is (1) or (2) as follows:

(1) the amino acid sequence of SEQ ID No:3 or SEQ ID No:13;

(2) an amino acid sequence obtained from substitution, addition or deletion of one or more amino acid residues of SEQ ID No:3 or SEQ ID No: 13 and having the same function;

the amino acid sequence of the heavy chain variable region CDR2 is (3) or (4) as follows:

(3) the amino acid sequence of SEQ ID No:4 or SEQ ID No: 14.

(4) an amino acid sequence obtained from substitution, addition or deletion of one or more amino acid residues of SEQ ID No:4 or SEQ ID No: 14 and having the same function;

the amino acid sequence of the heavy chain variable region CDR3 is (5) or (6) as follows:

(5) the amino acid sequence of SEQ ID No:5 or SEQ ID No:15;

(6) an amino acid sequence obtained from substitution, addition or deletion of one or more amino acid residues of SEQ ID No:5 or SEQ ID No: 15 and having the same function;

the amino acid sequence of the light chain variable region CDR1 is (7) or (8) as follows:

(7) the amino acid sequence of SEQ ID No:8 or SEQ ID No: 18;

(8) an amino acid sequence obtained from substitution, addition or deletion of one or more amino acid residues of SEQ ID No:8 or SEQ ID No: 18 and having the same function;

the amino acid sequence of the light chain variable region CDR2 is (9) or (10) as follows:

(9) the amino acid sequence of SEQ ID No:9 or SEQ ID No:19;

(10) an amino acid sequence obtained from substitution, addition or deletion of one or more amino acid residues of SEQ ID No:9 or SEQ ID No:19 and having the same function;

the amino acid sequence of the light chain variable region CDR3 is (11) or (12) as follows:

(11) the amino acid sequence of SEQ ID No: 10 or SEQ ID No:20;

(12) an amino acid sequence obtained from substitution, addition or deletion of one or more amino acid residues of SEQ ID No: 10 or SEQ ID No:20 and having the same function.

With respect to the above monoclonal antibodies, the anti-IFNAR1 monoclonal antibodies comprise a heavy chain variable region with an amino acid sequence of a1) or a2) as follows:

a1) the amino acid sequence of SEQ ID No:2 or SEQ ID No:12;

a2) an amino acid sequence obtained from substitution, addition or deletion of one or more amino acid residues of SEQ ID No:2 or SEQ ID No:12 and having the same function;

the anti-IFNAR1 monoclonal antibodies comprise a light chain variable region with an amino acid sequence of b1) or b2) as follows:

b1) the amino acid sequence of SEQ ID No:7 or SEQ ID No:17;

b2) an amino acid sequence obtained from substitution, addition or deletion of one or more amino acid residues of SEQ ID No:7 or SEQ ID No: 17 and having the same function.

With respect to the above monoclonal antibodies, the nucleotide sequence of the heavy chain variable region of the anti-IFNAR1 monoclonal antibody is c1) or c2) or c3):

c1) the DNA molecule of SEQ ID No:1 or SEQ ID No:11;

c2) a cDNA molecule or genomic DNA molecule having 75% or more than 75% identity with the nucleotide sequence of c1) and encoding the heavy chain variable region of the anti-IFNAR1 monoclonal antibody;

c3) a cDNA molecule or genomic DNA molecule capable of hybridizing with the nucleotide molecule of c1) or c2) under stringent condition, and encoding the heavy chain variable region of the anti-IFNAR1 monoclonal antibody;

the nucleotide sequence of the light chain variable region of the anti-IFNAR1 monoclonal antibody is of d1) or d2) or d3):

d1) the DNA molecule of SEQ ID No:6 or SEQ ID No:16;

d2) a cDNA molecule or genomic DNA molecule having 75% or more than 75% identity with the nucleotide sequence of d1) and encoding the light chain variable region of the anti-IFNAR1 monoclonal antibody;

d3) a cDNA molecule or genomic DNA molecule capable of hybridizing with the nucleotide molecule of d1) or d2) under stringent condition, and encoding the heavy chain variable region of the anti-IFNAR1 monoclonal antibody.

The antibodies provided herein comprise a heavy and a light chain variable region comprising an amino acid sequence homologous to an amino acid sequence of the above antibodies, and the antibodies retain the functional properties of the anti-IFNAR1 antibodies provided herein. For example, the present disclosure provides an isolated monoclonal antibody or antigen-binding portion thereof, comprising a heavy chain variable region and a light chain variable region, wherein:

(a) the heavy chain variable region comprises an amino acid sequence that is at least 80% homologous to an amino acid sequence selected from SEQ ID No:2 and SEQ ID No:12;
(b) the light chain variable region comprises an amino acid sequence that is at least 80'/homologous to an amino acid selected from SEQ ID No:7 and SEQ ID No: 17;
(c) the antibody specificity binds to IFNAR1 and exhibits at least one of the functional properties described below:
L1: inhibiting the biological activity of type I interferons in type I interferon signaling reporter cells;
L2: inhibiting the expression of interferon effector gene mx2 in CpGA stimulated human peripheral blood mononuclear cells;
L3: inhibiting the expression of interferon effector gene mx2 in IFNα2b stimulated human peripheral blood mononuclear cells;
L3: inhibiting the expression of interferon effector gene mx2 in R848 stimulated human peripheral blood mononuclear cells;
L5: inhibiting the expression of interferon effector gene isg15 in CpGA stimulated human peripheral blood mononuclear cells;
L6: inhibiting the expression of interferon effector gene isg15 in IFNα2b stimulated human peripheral blood mononuclear cells;
L7: inhibiting the expression of interferon effector gene isg15 in R848 stimulated human peripheral blood mononuclear cells.

The VH and/or VL amino acid sequences of the antibodies provided herein may be 85%, 90%, 95%, 96%, 97%, 98% or 99% homologous to the sequences set forth above. The percent homology between two amino acid sequences is equivalent to the percent identity between the two sequences. The percent identity between the two sequences is a function of the number of identical positions shared by the sequences (i.e., % homology=number of identical positions/total number of positions×100%), taking into account the number of gaps, and the length of each gap, which need to be introduced for optimal alignment of the two sequences.

The antibodies provided herein are characterized by particular functional features or properties of antibodies. For example, the antibodies bind specifically to IFNAR-1, preferably human IFNAR-1. Additionally, the antibodies may cross react with IFNAR-1 from one or more non-human primates, such as cynomolgus monkey and/or rhesus monkey.

Furthermore, the antibodies provided herein are capable of inhibiting the biological activity of type 1 interferons. The antibodies inhibit the biological activity of at least one type I interferon, and preferably inhibit the biological activity of multiple type I interferons (i.e., at least two, more preferably at least three, or at least four, or at least five, or at least six, or at least seven, or at least eight, or at least nine, or at least ten, or at least 11, or at least 12, or at least 13 or at least 14 or at least 15, different subtypes of type I interferon). In a preferred embodiment, the antibodies inhibit the biological activity of the following type I interferons: α1, α2a, α2b, α4, α5, α6, α7, α8, α10, α14, α16, α17, α21, β and ω. In other preferred embodiments, the antibodies inhibit the biological activity of type I interferons in agonists stimulated human peripheral blood mononuclear cells.

The ability of an antibody to inhibit the biological activity of type I interferons can be determined in one or more assays established in the art. Non-limiting examples include inhibition of biological activity of type I interferons in type I interferon signaling reporter cells, inhibition of expression of interferon effector genes (e.g.: mx2 and isg15S), in human peripheral blood mononuclear cells (PBMCs) simulated by agonists such as CpG, IFN α2b or R848. An antibody "inhibits the biological activity of type I interferons" if it inhibits the activity by at least 2⁰%, more preferably by at least 30%, even more preferably by at least 40%, at least 50%, at least 60, at least 70%, at least 80% or at least 90%, as compared to a non-specific, control antibody.

In preferred embodiments, the antibodies inhibit the biological activity of IFNα2b in type I interferons signaling HEK293T reporter cells, and inhibit the expression of interferon effector genes such as mx2 and isg15, in human peripheral blood mononuclear cells stimulated by agonists such as CpG, IFN α2b or R848.

In one aspect, the preferred antibodies provided herein are the monoclonal antibodies 10C2 and 10C9, isolated and structurally characterized as described in the Examples. The VH amino acid sequences of 10C2 and 10C9 are shown in SEQ ID NOs: 2 and 12, respectively. The VL amino acid sequences of 10C2 and 10C9 are shown in SEQ ID NOs: 7 and 17, respectively.

Given that each of these antibodies can bind to IFNAR1, the VH and VL sequences can be "mixed and matched" to create other anti-IFNAR1 binding molecules of the disclosure. IFNAR1 binding of such "mixed and matched" antibodies can be tested using the binding assays described herein and/or using the type I IFN functional inhibition assays described in the Examples. Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. For example, the VH and VL sequences of 10C2 and 10C9 are particularly amenable for mixing and matching, since these antibodies use VH and VL sequences derived from the same germline sequences (IGHV9-3 and IGKV6-13) and thus they exhibit structural similarity.

In another aspect, the disclosure provides antibodies that comprise the heavy chain and light chain CDR1s, CDR2s and CDR3s of 10C2 and 10C9, or combinations thereof. The amino acid sequences of the VH CDR1s of 10C2 and 10C9 are shown in SEQ ID NOs: 3 and 13. The amino acid sequences of the VH CDR2s of 10C2 and 10C9 are shown in SEQ ID NOs: 4 and 14. The amino acid sequences of the VH CDR3s of 10C2 and 10C9 are shown in SEQ ID NOs: 5 and 15. The CDR regions are labelled by Vector NTI Software.

Given that each of these antibodies can bind to IFNAR1 and that antigen-binding specificity is provided primarily by the CDR1, CDR2 and CDR3 regions, the VH CDR1, CDR2 and CDR3 sequences and VL CDR1, CDR2 and CDR3 sequences can be "mixed and matched" (i.e., CDRs from different antibodies can be mixed and matched, but each antibody must contain a VH CDR1, CDR2 and CDR3 and a VL CDR1, CDR2 and CDR3) to create other anti-IFNAR1 binding molecules of the disclosure. IFNAR-1 binding of such "mixed and matched" antibodies can be tested using the binding assays described above and in the Examples. Preferably, when VH CDR sequences are mixed and matched, the CDR1, CDR2 and/or CDR3 sequence from a particular VH sequence is replaced with a structurally similar CDR sequence (s). Likewise, when VL CDR sequences are mixed and matched, the CDR1, CDR2 and/or CDR3 sequence from a particular VL sequence preferably is replaced with a structurally similar CDR sequence(s). For example, the VH CDR1s of 10C2 and 10C9 share some structural similarity and therefore are amenable to mixing and matching. It will be readily apparent to the ordinarily skilled artisan that novel VH and VL sequences can be created by substituting one or more VH and/or VL CDR region sequences with structurally similar sequences from the CDR sequences disclosed herein for monoclonal antibodies 10C2 and 10C9.

In certain embodiments, an antibody of the disclosure comprises a heavy chain variable region from a particular germline heavy chain immunoglobulin gene and/or a light chain variable region from a particular germline light chain immunoglobulin gene.

For example, in a preferred embodiment, the disclosure provides an isolated anti-IFNAR-1 monoclonal antibody, or an antigen-binding portion thereof, wherein the antibody:

(a) comprises a heavy chain variable region of mouse IGHV9-3, IGHD2-13 and IGHJ1 gene, or IGHV9-3, IGHD1-1 and IGHJ3 gene;

(b) comprises a light chain variable region of mouse IGKV6-13 and IGKJ5 gene or IGKV6-15 and IGKJ2 gene;

and (c) the antibody specifically binds to IFNAR-1.

Example of antibodies having VH of IGHV9-3, IGHD2-13 and IGHJ1, and VL of IGKV6-13 and IGKJ5 is 10C2. Example of antibodies having VH of IGHV9-3, IGHD1-1 and IGHJ3, and VL of IGKV6-15 and IGKJ2 is 10C9.

As used herein, an antibody comprises heavy or light chain variable regions "of" or "derived from" or "the product of" a particular germline sequence if the variable regions of the antibody are obtained from a system that uses mouse germline immunoglobulin genes. A mouse antibody that is "of" or "derived from" or "the product of" a mouse germline immunoglobulin sequence can be identified as such by comparing the amino acid sequence of the mouse antibody with the amino acid sequences of mouse germline immunoglobulins and selecting the mouse germline immunoglobulin sequence that is closest in sequence (i.e., greatest % identity) to the sequence of the mouse antibody. A mouse antibody that is "of" or "derived from" or "the product of" a particular mouse germline immunoglobulin sequence may contain amino acid differences as compared to the germline sequence, due to, for example, naturally-occurring somatic mutations or intentional introduction of site-directed mutation. However, a selected mouse antibody typically is at least 90% identical in amino acids sequence to an amino acid sequence encoded by a mouse germline immunoglobulin gene and contains amino acid residues that identify the mouse antibody as being mouse when compared to the germline immunoglobulin amino acid sequences of other species (e. g., murine germline sequences).

In certain cases, a mouse antibody may be at least 95%, or even at least 96%, 97%, 98%, or 99% identical in amino acid sequence to the amino acid sequence encoded by the germline immunoglobulin gene. Typically, a mouse antibody derived from a particular mouse germline sequence will display no more than 10 amino acid differences from the amino acid sequence encoded by the mouse germline immunoglobulin gene. In certain cases, the mouse antibody may display no more than 5, or even no more than 4, 3, 2, or 1 amino acid difference from the amino acid sequence encoded by the germline immunoglobulin gene.

The Second Objective of the Disclosure is to Provide Hybridoma Cells which Express the Anti-IFNAR1 Monoclonal Antibodies.

The hybridoma cells provided herein have a deposit number of CGMCC deposit No. 12542 or CGMCC deposit No. 12543.

The hybridoma cells thereof were named as hybridoma cell line 10C2 and hybridoma cell line 10C9.

The taxonomic nomenclature of the hybridoma cell line 10C2 is mouse hybridoma cell line, which is deposited with China General Microbiological Culture Collection Center (CGMCC, address: No. 3, 1st courtyard, Beichen West Road, Chaoyang District, Beijing 100101, China), and the deposit No. is CGMCC No. 12542.

The taxonomic nomenclature of the hybridoma cell line 10C9 is mouse hybridoma cell line, which is deposited with China General Microbiological Culture Collection Center (CGMCC, address: No. 3, 1st courtyard, Beichen West Road, Chaoyang District, Beijing 100101, China), and the deposit No. is CGMCC No. 12543.

The Third Objective of the Disclosure is to Provide New Uses of Anti-IFNAR1 Monoclonal Antibodies or Antigen-Binding Portion Thereof, or the Hybridoma Cell Lines Thereof.

This present disclosure provides at least one use of anti-IFNAR1 monoclonal antibodies or antigen-binding portions thereof, or the hybridoma cell lines thereof in A) to G):

A) binding to human IFNAR1;

B) inhibiting biological activity of type I interferons;

C) inhibiting biological activity of IFNα2b;

D) binding to SD2 domain and/or SD3 domain;

E) inhibiting biological activity of type I interferons in type I interferon signaling reporter cells;

F) inhibiting the biological activity of type I interferons in agonist stimulated human peripheral blood mononuclear cells;

G) treatment and/or prevention of type I interferon-mediated disease and/or diseases caused by type I interferon abnormality.

Among the above uses, said inhibiting biological activity of type I interferons in agonist stimulated human peripheral blood mononuclear cells thereof is embodied in (1)-(6) as follows:

(1) inhibiting expression of interferon effector gene mx2 in CpGA stimulated human peripheral blood mononuclear cells;

(2) inhibiting expression of interferon effector gene mx2 in IFNα2b stimulated human peripheral blood mononuclear cells;

(3) inhibiting expression of interferon effector gene mx2 in R848 stimulated human peripheral blood mononuclear cells;

(4) inhibiting expression of interferon effector gene isg15 in CpGA stimulated human peripheral blood mononuclear cells;

(5) inhibiting the expression of interferon effector gene isg15 in IFNα2b stimulated human peripheral blood mononuclear cells;

(6) inhibiting the expression of interferon effector gene isg15 in R848 stimulated human peripheral blood mononuclear cells.

Among the above uses, the type I interferon is IFNα.

The Fourth Objective of the Disclosure is to Provide an Antagonist of Type I Interferon.

The present disclosure provides a type I interferon antagonist having an active ingredient which is the above disclosed anti-IFNAR1 monoclonal antibody or the antigen-binding portion thereof.

The Fifth Purpose of the Disclosure is to Provide a Composition.

The present disclosure provides a composition, e.g., a pharmaceutical composition, comprising one or a combination of monoclonal antibodies, or the antigen-binding portion(s) thereof provided herein, formulated together with a pharmaceutically acceptable carrier. Such a composition may include one or a combination of (e. g., two or more different) antibodies, or immunoconjugates or bispecific molecules provided herein. For example, a pharmaceutical composition provided herein can comprise a combination of antibodies (or immunoconjugates or bispecific agents) that bind to different epitopes on the target antigen or that have complementary activities.

Pharmaceutical compositions provided herein also can be administered in combination therapy, i.e., combined with other agents. For example, the combination therapy can include an anti-IFNAR-I antibody provided herein combined with at least one additional immunosuppressing agent. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e. g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds provided herein may include one or more pharmaceutically acceptable salts. A "pharmaceutically acceptable salt" refers to a salt that retains the desired biological activity of the parent compound and does not impart any undesired toxicological effects (see e. g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures as described, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about 99 percent of active ingredient, preferably from about 0.1 percent to about 70 percent, most preferably from about 1 percent to about 30 percent of active ingredient in combination with a pharmaceutically acceptable carrier.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of the disclosure include intravenous, intramuscular, intradermal, intraperitoneal, subcutaneous, spinal or other parenteral routes of administration, for example by injection or infusion.

The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Alternatively, an antibody of the disclosure can be administered via a non-parenteral route, such as a topical, epidermal or mucosal route of administration, for example, intranasally, orally, vaginally, rectally, sublingually or topically.

The antibodies (and immunoconjugates and bispecific molecules) provided herein have in vitro and in vivo diagnostic and therapeutic utilities. For example, these molecules can be administered to cells in culture, e. g. in vitro or ex vivo, or in a subject, e. g., in vivo, to treat, prevent or diagnose a variety of disorders.

The term "subject" as used herein in intended to include human and non-human animals. Non-human animals includes all vertebrates, e. g., mammals and non-mammals, such as non-human primates, sheep, dogs, cats, cows, horses, chickens, amphibians, and reptiles. The methods are particularly suitable for treating human patients having a disorder associated with aberrant or inappropriate Type I interferon expression (e. g., overexpression).

When the anti-IFNAR-1 antibodies are administered together with another agent, the two can be administered in either order or simultaneously. For example, an anti-IFNAR-1 antibody of the disclosure can be used in combination with one or more of the following agents: anti-IFNa antibody, anti-IFN-γ receptor antibody, soluble IFN-γ receptor, anti-TNF antibody, anti-TNF receptor antibody and/or soluble TNF receptor. Furthermore, an anti-IFNAR-1 antibody of disclosure can be used in combination with a Flt3 ligand antagonist.

The Sixth Objective of the Present Disclosure is to Provide an Immunoconjugate.

The present disclosure provides an immunoconjugate containing the anti-IFNAR-1 monoclonal antibodies, or antigen-binding portion (s) of the present disclosure.

The immunoconjugate contains a pharmaceutically acceptable carrier.

The anti-IFNAR-1 antibody, or a fragment thereof provided herein can be conjugated to a therapeutic moiety, such as a cytotoxin, a drug (e. g., an immunosuppressant) or a radiotoxin, to obtain conjugates. Such conjugates are referred to herein as "immunoconjugates". Immunoconjugates that include one or more cytotoxins are referred to as "immunotoxins". A cytotoxin or cytotoxic agent includes any agent that is detrimental to (e. g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e. g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e. g., daunorubicin (formerly daunomycin) and doxorubicin), antibiotics (e. g., dactinomycin (formerly actinomycin), bleomycin, mithramycin, and anthramycin (AMC)), and anti-mitotic agents (e. g., vincristine and vinblastine). Other preferred examples of therapeutic cytotoxins that can be conjugated to an antibody of the disclosure include duocarmycins, calicheamicins, maytansines and auristatins, and derivatives thereof.

Cytoxins can be conjugated to antibodies provided herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55: 199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Currt. Opin. Investig. Drugs 3:1089-1091; Senter, P. D. and Springer, C. J. (2001) Adv. Drug Deliv. Rev. 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttriumg$^{90}$ and lutetium$^{77}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies provided herein.

The antibody conjugates provided herein can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies' 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

The Seventh Objective of the Present Disclosure is to Provide a Genetically Engineered Antibody.

The genetically engineered antibody of the present disclosure is an antibody obtained from modifying and engineering the above disclosed IFNAR1 monoclonal antibody or antigen binding portion thereof.

In certain embodiments, the antibody provided herein comprises a heavy chain variable region comprising CDR1, CDR2 and CDR3 sequences and a light chain variable region comprising CDR1, CDR2 and CDR3 sequences, wherein one or more of these CDR sequences comprise a specified amino acid sequences based on the preferred antibodies described herein (e.g., 10C2 and 10C9), or conservative modifications thereof, and wherein the antibodies retain the desired functional properties of the anti-IFNAR-1 antibodies provided herein. Accordingly, the present disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein: the heavy chain variable region CDR3 sequence comprises an amino acid sequence selected from the group consisting of amino acid sequences of SEQ ID NOs: 5 and 15, and conservative modifications thereof; and the light chain variable region CDR3 sequence comprises an amino acid sequence selected from the group consisting of amino acid sequences of SEQ ID NOs: 10 and 20, and conservative modifications thereof; and the antibody specifically binds to IFNAR-1 and exhibits at least one of the functional properties described herein.

In a further embodiment, the heavy chain variable region CDR2 sequence comprises an amino acid sequence selected from the group consisting of amino acid sequences of SEQ ID NOs: 4 and 14, and conservative modifications thereof, and the light chain variable region CDR2 sequence comprises an amino acid sequence selected from the group consisting of amino acid sequences of SEQ ID NOs: 9 and 19, and conservative modifications thereof. In a still further embodiment, the heavy chain variable region CDR1 sequence comprises an amino acid sequence selected from the group consisting of amino acid sequences of SEQ ID NOs: 3 and 13, and conservative modifications thereof, and the light chain variable region CDR1 sequence comprises an amino acid sequence selected from the group consisting of amino acid sequences of SEQ ID NOs: 8 and 18, and conservative modifications thereof.

As used herein, the term "conservative modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e. g., lysine, arginine, histidine), acidic side chains (e. g., aspartic acid, glutamic acid), uncharged polar side chains (e. g., glycine, asparagine, glutamine, serine, threonine, tyrosine, cysteine, tryptophan), nonpolar side chains (e. g., alanine, valine, leucine, isoleucine, proline, phenylalanine, methionine), beta-branched side chains (e. g., threonine, valine, isoleucine) and aromatic side chains (e. g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i. e., the functions set forth in (c), (d) and (e) above) using the functional assays described herein.

An antibody provided herein can also be prepared using an antibody having one or more of the VH and/or VL sequences disclosed herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Alternatively, an antibody can be engineered by modifying residues within the constant region (s), example to alter the effector function (s) the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e. g., Riechmann, L. et al. (1998) Nature 332: 323-327; Jones, P. et al. (1986) Nature 321:522-525; Queen, C. et al. (1989) Proc. Natl. Acad. See. U.S.A. 86: 10029-10033).

Accordingly, another embodiment of the present disclosure pertains to an isolated monoclonal antibody, or antigen binding portion thereof, comprising: a heavy chain variable region comprising CDR1, CDR2, and CDR3 sequences comprising an amino acid sequence selected from the group consisting of SEQ ID NOs: 3 and 13, SEQ ID NOs: 4 and 14 and SEQ ID NOs: 5 and 15, respectively, and a light chain variable region comprising CDR1, CDR2, and CDR3 sequences comprising an amino acid sequence selected from the group consisting of SEQ ID NOs: 8 and 18, SEQ ID NOs: 9 and 19 and SEQ ID NOs: 10 and 20, respectively. Thus, such antibodies contain the VH and VL CDR sequences of monoclonal antibodies 10C2 or 10C9 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U. S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J. Immunol. 24: 827-836.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation (s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions.

Moreover, typically no more than five residues are altered within a CDR region are altered.

Accordingly, in another embodiment, the disclosure provides isolated anti-IFNAR-1 monoclonal antibodies, or antigen binding portions thereof, comprising a heavy chain variable region comprising:

(a) a VH CDR1 region comprising an amino acid sequence selected from the group consisting of SEQ ID NO: 3 and 13, or an amino acid sequence having one, two, three, four or five amino acid substitutions, deletions or additions as compared to an amino acid sequence selected from the group consisting of SEQ ID NO: 3 and 13;

(b) a VH CDR2 region comprising an amino acid sequence selected from the group consisting of SEQ ID NO: 4 and 14, or an amino acid sequence having one, two, three, four or five amino acid substitutions, deletions or additions as compared to an amino acid sequence selected from the group consisting of SEQ ID NO: 4 and 14;

(c) a VH CDR3 region comprising an amino acid sequence selected from the group consisting of SEQ ID NO: 5 and 15, or an amino acid sequence having one, two, three, four or five amino acid substitutions, deletions or additions as compared to an amino acid sequence selected from the group consisting of SEQ ID NO: 5 and 15;

(d) a VL CDR1 region comprising an amino acid sequence selected from the group consisting of SEQ ID NO: 8 and 18, or an amino acid sequence having one, two, three, four or five amino acid substitutions, deletions or additions as compared to an amino acid sequence selected from the group consisting of SEQ ID NO: 8 and 18;

(e) a VL CDR2 region comprising an amino acid sequence selected from the group consisting of SEQ ID NO: 9 and 19, or an amino acid sequence having one, two, three, four or five amino acid substitutions, deletions or additions as compared to an amino acid sequence selected from the group consisting of SEQ ID NO: 9 and 19;

(f) a VL CDR3 region comprising an amino acid sequence selected from the group consisting of SEQ ID NO: 10 and 20, or an amino acid sequence having one, two, three, four or five amino acid substitutions, deletions or additions as compared to an amino acid sequence selected from the group consisting of SEQ ID NO: 10 and 20.

Engineered antibodies of the present disclosure include those in which modifications have been made to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody.

In addition to modifications made within the framework or CDR regions, antibodies of the present disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present disclosure may be chemically modified (e. g., one or more chemical moieties can be attached to the antibody) or be modified to alter its glycosylation, again to alter one or more functional properties of the antibody.

The structural features of anti-IFNAR-1 antibodies of the present disclosure, e. g. 10C2 and 10C9 are used to create structurally related anti-IFNAR-1 antibodies that retain at least one functional property of the antibodies of the disclosure, such as binding to IFNAR-1. For example, one or more CDR regions of 10C2 and 10C9 can be combined recombinantly with known framework regions and/or other CDRs to create additional, recombinantly-engineered, anti-IFNAR-1 antibodies of the disclosure. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence (s) can be used as the starting material to create a "second generation" sequence(s) from the original sequence(s), then the "second generation" sequence (s) can be prepared and expressed as a protein.

The above methods for preparing an engineered anti-IFNAR-1 antibody comprising:

(a) providing: (i) a heavy chain variable region antibody sequence comprising a CDR1 sequence selected from SEQ ID NO: 3 and 13, a CDR2 sequence selected from SEQ ID NO: 4 and 14 and a CDR3 sequence selected from SEQ ID NO: 5 and 15; and (ii) a light chain variable region antibody sequence comprising a CDR1 sequence selected from SEQ ID NO: 8 and 18, a CDR2 sequence selected from SEQ ID NO: 9 and 19 and a CDR3 sequence selected from SEQ ID NO: 10 and 20;

(b) altering at least one amino acid residue within the first antibody sequence and/or the second antibody sequence to create at least one altered antibody sequence; and (c) preparing the altered antibody sequence; and (d) expressing the altered antibody sequence as a protein.

Standard molecular biology techniques can be used to prepare and express the altered antibody sequence. Preferably, the antibody encoded by the altered antibody sequence (s) one that retains one, some or all of the functional properties of the anti-IFNAR-1 antibodies described herein, which functional properties include, but are not limited to: binding to IFNAR-1; inhibiting the binding of type I interferons to IFNAR-1; binding to cells expressing human IFNAR-1; inhibiting the biological activity of IFNAR-1 on cells expressing human IFNAR-1; inhibiting the biological activity on PBMCs stimulated with stimulant.

The functional properties of the altered antibodies can be assessed using standard assays available in the art and/or described herein.

In certain embodiments of the methods of engineering antibodies of the present disclosure, mutations can be introduced randomly or selectively along all or part of an anti-IFNAR-1 antibody coding sequence (e. g., 10C2 or 10C9 coding sequence) and the resulting modified anti-IFNAR-1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof.

The Eighth Objective of the Present Disclosure is to Provide a Humanized Antibody.

The present disclosure provides a humanized antibody obtained from humanizing anti-IFNAR-1 monoclonal antibodies, or antigen-binding portion (s) of the present disclosure.

A monoclonal antibody of the present disclosure may be humanized, or prepared as chimeric antibodies recombinant DNA techniques known in the art. Mouse variable region may be linked to human constant region using methods known in the art. A variety of approaches for making chimeric antibodies have been described. See e.g., Morrison et ah, Proc. Natl. Acad. ScL U.S.A. 81:6851, 1985; Takeda et al, Nature 314:452, 1985, Cabilly et al, U.S. Pat. No. 4,816,567; Boss et al, U.S. Pat. No. 4,816,397; Tanaguchi et al., European Patent Publication EP171496; European Patent Publication 0173494, United Kingdom Patent GB 2177096B, the disclosures of which are incorporated herein by reference in their entirety. Humanizing an antibody involves transplanting the combining-site of a nonhuman antibody onto a human antibody. This may be performed by grafting the nonhuman CDRs onto human framework and human constant regions or by transplanting the entire non-human variable domains but hiding them with a human-like surface by replacement of certain exposed residues. Details on creating a humanized antibody are disclosed in U.S. Pat. No. 5,472,693.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4: 214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or back-mutations. Such altered immunoglobulin molecules can be made by any of several techniques known in the art, (e.g., Teng et al, Proc. Natl. Acad. ScL U.S.A., 80: 7308-7312, 1983; Kozbor et al, Immunology Today, 4: 7279, 1983; Olsson et al, Meth. Enzymol, 92: 3-16, 1982). Typically, conservative substitutions are made. Often, but not exclusively, an amino acid common to a position in human germline antibody sequences may be used. Human germline sequences, e.g., are disclosed in Tomlinson, et al (1992) J. MoL Biol. 227:776-798; Cook, G. P. et al (1995) Immunol. Today Vol. 16 (5): 237-242; Chothia, D. et al (1992) J. Mol Biol. 227:799-817; and Tomlinson et al (1995) EMBO J. 14: 4628-4638. These sequences can be used as a source of human sequence, e.g., for framework regions and CDRs.

Human antibodies can be generated using methods known in the art, such as phage display technology. Phage display technology mimics the mammalian immune system by cloning large libraries of antibody genes and selecting for binding to a desired target, such as the epitopes in SD2, SD3 of IFNAR1. The libraries used in phage display technology can be made from several sources. For example, an immune library, created from humans exposed to a desired antigen through vaccination or disease, has high levels of circulating antibodies to the antigen even when the library is relatively small. As another example, a naive library, made from mRNA isolated from non-immunized individuals, can be used repeatedly to isolate antibodies against a variety of antigens. As still another example, a synthetic library, in which germline antibody gene segments are cloned and arranged combinatorically in vitro to reconstitute genes encoding complete VH and VL chains, has the advantage of producing antibodies with specificity to self-antigens. Semisynthetic libraries can also be made by selecting one or more antibody frameworks and randomizing sequences within the CDR loops.

In phage display technology, once a library is created, it is fused to a surface protein of phages. In a process known as panning, phages displaying an antibody specific for the antigen of interest are enriched by selective adsorption onto immobilized antigen. Subsequently, the bound phage can be eluted from the surface and amplified through infection of *E. coli* cells.

Other modifications of phage display technology to generate human antibodies are also known in the art. For example, antibodies can be displayed on the surfaces of microbial cells, such as *E. coli* and *Saccharomyces* cerevisaie, instead of on the surface of bacteriophages. In this case, screening can be performed by incubation with a fluorescently tagged ligand in buffer. Cells that display the antibodies that bind to the ligand become fluorescently labeled and are isolated by fluorescence-activated cell sorting. Another modification, termed ribosome display, relies on the formation of a ternary complex between ribosomes, mRNA, and the polypeptide.

Another method known in the art to produce human antibodies is one that uses transgenic mice. The native immunoglobulin repertoire in these mice has been replaced with human V-genes in the murine chromosome. The mice can be injected with a desired antigen and the resulting antibodies can be recovered by cloning and screening an immune library, or by conventional hybridoma technology. These mice produce significant levels of fully human antibodies that only differ in glycosylation patterns.

The Ninth Objective of the Present Disclosure is to Provide a Bispecific Molecule.

The present disclosure provides a bispecific molecule comprising the above IFNAR1 monoclonal antibody or antigen-binding portions thereof.

The present disclosure provides bispecific molecules comprising specific binding sites of the above disclosed anti-IFNAR-1 monoclonal antibodies, or the antigen-binding portions thereof, wherein the antibodies or the antigen-binding portions thereof provided herein can be derivatized or linked to another functional molecule, e.g., another peptide or protein (e.g., another antibody or ligand for a receptor) to generate a bispecific molecule that binds to at least two different binding sites or target molecules. The antibody of the present disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the disclosure, an antibody of the disclosure can be functionally linked (e. g., by chemical coupling, genetic fusion, noncovalent association or otherwise) to one or more other binding molecules, such as another antibody, antibody fragment, peptide or binding mimetic, such that a bispecific molecule results.

The Tenth Objective of the Present Disclosure is to Provide Biomaterials Related with the Above Disclosed Monoclonal Antibody of IFNAR1, or Antigen-Binding Portion Thereof.

The biomaterials related to the above disclosed monoclonal antibody of IFNAR1, or antigen-binding portion thereof are any of A1) to A12) as follows:

A1) the nucleic acid molecule encoding the IFNAR1 monoclonal antibody, or antigen-binding portion thereof;

A2) an expression kit comprising the nucleic acid molecule of A1);

A3) an expression vector comprising the nucleic acid molecule of A1);

A4) an expression vector comprising the expression kit of A2);

A5) a modified microorganism comprising the nucleic acid molecule of A1);

A6) a modified microorganism comprising the expression kit of A2);

A7) a modified microorganism comprising the expression vector of A3);

A8) a modified microorganism comprising the expression vector of A4);

A9) a transgenic cell line comprising the nucleic acid molecule of A1);

A10) a transgenic cell line comprising the expression kit of A2);

A11) a transgenic cell line comprising the expression vector of A3);

A12) a transgenic cell line comprising the expression vector of A4).

The nucleic acid molecules may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the present disclosure can be, for example, DNA or RNA and may or may not contain intronic sequences. In a preferred embodiment, the nucleic acid is a cDNA molecule.

Nucleic acids of the present disclosure can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e. g., using phage display techniques), nucleic acid encoding the antibody can be recovered from the library.

Preferred nucleic acids molecules of the present disclosure are those encoding the VH and VL sequences of the 10C2 and 10C9 monoclonal antibodies. DNA sequences encoding the 10C2 VH and VL sequences are shown in SEQ ID NOs: 1 and 6, respectively. DNA sequences encoding the 10C9 VH and VL sequences are shown in SEQ ID NOs: 11 and 16, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VH and/or VL encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CHI, CH2 and CH3). The sequences of human heavy chain constant region genes are known in the art (see e.g., Kabat, B. A., et al. (1991) Sequences of Proteins of Immunological Interest, Fifth Edition, U. S. Department of Health and Human Services, NIH Publication No. 91-3242) and DNA fragments encompassing these regions can be obtained by standard PCR amplification. The heavy chain constant region can be an IgG1, lgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CHI constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, B. A., et al. (1991) Sequences of Proteins of Immunological Interest, Fifth Edition, U. S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e. g., encoding the amino acid sequence (Gly4-Ser) 3, such that the VH and VL sequences can be expressed as a contiguous single-chain protein, with the VL and VH regions joined by the flexible linker (see e. g., Bird et al. (1988) Science 242: 423-426; Huston et al. (1988) Proc. Natl. Acad. Sci. USA 85: 5879-5883; McCafferty et al., (1990) Nature 348: 552-554).

The Eleventh Objective of the Present Disclosure is to Provide a Method for Production of Anti IFNAR1 Antibody.

The method for production of anti IFNAR1 antibody, comprising:

1) providing (i) a sequence of the heavy chain variable region of the antibody, comprising CDR1 sequence selected from SEQ ID No:3 and SEQ ID No:13, CDR2 sequence selected from SEQ ID No:4 and SEQ ID No:14, and CDR3 sequence selected from SEQ ID No:5 and SEQ ID No:15, or (ii) a sequence of the light chain variable region of the antibody, comprising CDR1 sequence selected from SEQ ID No:8 and SEQ ID No:18, CDR2 sequence selected from SEQ ID No:9 and SEQ ID No:19, and CDR3 sequence selected from SEQ ID No:10 and SEQ ID No:20, 2) altering at least one amino acid residue in at least one of the antibody variable region sequence, wherein the sequence is selected from the sequence of the heavy variable region and the sequence of the light chain variable region, thereby producing at least one altered antibody sequence;

3) expressing the altered antibody sequence as a protein.

The monoclonal antibody of the present disclosure is prepared from the standard monoclonal antibody preparation method (for example, Paterson, H.M.V.a.Y. (Jone Wiley and Sons, Inc. New York, 1995). Production of Antibodies. Current Protocols in Immunology). The animal for preparing hybridomas is preferably mouse. The procedure of using a mouse to produce hybridomas is well established. The immunization procedure and the techniques of isolation of immunized spleen cells are known in the art. Fusion partner (for example, mouse myeloma cells) and fusion methods are also well known.

In the procedure of mouse immunization for preparing the monoclonal antibodies of the present disclosure, the mouse may be immunized with pure or enriched IFNAR1 antigen formulation and/or IFNAR1 expressing cells. Preferably, the mouse is immunized with IFNAR1 expressing mouse cells. The mouse is 6-8 weeks of age for the first injection. For example, mouse may be immunized with pure or enriched IFNAR1 antigen formulation (5-50 g) intraperitoneally, or immunized with IFNAR1 expressing mouse cells, preferably, immunized with mixture of IFNAR1 expressing mouse cells and immunologic adjuvant, such as CpG-B intraperitoneally to boost immune response. Mice may be immunized several times, for example, three, four or five times, at intervals of three or four weeks. Three days, four or five days after the last immunization, mouse spleen cells or lymph node cells can be taken and fused with mouse myeloma cells.

In the procedures for preparing the hybridoma cells of the monoclonal antibody of the present disclosure, spleen cells and/or lymph node cells may be isolated from the immunized mice, and fused with suitable immortal cell lines, such as mouse myeloma cell lines. Hybridoma may be screened and obtained according to production of antigen specific antibody. For example, single cell suspension of spleen lymphocytes from immunized mouse may be fused with one third number of mouse myeloma SP2/0. About $2 \times 10^5$ cells are inoculated into flat bottom microtiter plate, and incubated in selective medium which contains 10% fetal bovine serum, 4 mL-glutamine, 1 mM sodium pyruvate, 5 mm HEPES, 50 units/mL penicillin, 50 mg/mL streptomycin and I xHAT (Sigma; HAT was added 24 hours later) for 10 days. About 10 days later, hybridoma cells are screened for secretion of IFNAR1 antibody.

In procedures for screening of hybridoma cells for producing monoclonal antibodies of the present disclosure, a eukaryotic expression vector expressing extracellular domain of human IFNAR1 is constructed and transfected HEK293T cell line to obtain a reporter cell line for screening IFNAR1 antibody secreted by hybridoma cells, in which the cell line stably express GFP. If the hybridoma cells secrete IFNAR1 antibodies, and the antibodies bind to the extracellular domain of the IFNAR1 expressed on the cells, then the cells may emit green fluorescence and yellow fluorescence after adding PE-labelled anti-mouse IgG antibody. Hybridoma secreting IFNAR1 antibody can be screened by analyzing GFP and PE signals of cells by flow cytometry. Monoclonal IgG antibodies of each well were screened by a reporter cell line stably expressing the extracellular domain of IFNAR1. Once extensive hybridoma growth occurs, hybridoma cells are usually screened after 10-14 days. Hybridoma cells secreting IFNAR1 antibody are subcloned by limited dilution method and were screened again. If still positive for human IFNAR1, then the monoclonal antibody is subcloned at least twice by limited dilution. Then the stable subclones are cultured in vitro, and a small amount of antibodies are produced in tissue culture medium for characterization.

To purify monoclonal antibodies, the selected hybridomas can be grown in two-liter spinner-flasks for monoclonal antibody purification. Supernatants can be filtered and concentrated before affinity chromatography with Nab Protein G Spin Column (GE). Eluted IgG can be checked by gel electrophoresis and high performance liquid chromatography to ensure purity. Concentration of the antibody may be determined by BCA protein quantification method (Pierce). The monoclonal antibodies can be divided into aliquots and stored at −80° C.

To test whether the monoclonal antibodies that are identified as binding to IFNAR1-expressing cells can prevent the binding of type I interferon and block the ability of downstream signal transduction, the supernatant of hybridoma culture is incubated with the reporter cells constructed as described herein of type I interferon signal at 37° C. for 30 minutes to 2 hours, preferably 30 minutes, 1 hour, 2 hours, more preferably 1 hour, and then adding type I interferon at an appropriate amount, for example, 1 ng/ml to 1 μg/ml, preferably 1 ng/ml to 500 ng/ml, further preferably 1 ng/ml to 100 ng/ml, specifically 1 ng/ml, 10 ng/ml, 20 ng/ml, 30 ng/ml, 40 ng/ml, 50 ng/ml, more preferably 10 ng/ml. The cells were further incubated for a certain period of time, for example, 18-36 hours, preferably 20-28 hours, more preferably 24 hours. GFP expression in the reporter cells was analyzed by flow cytometry. Samples showing low GFP expression in cells are antibodies that block type I interferon receptor. By using the above method, antibodies such as 10C2 and 10C9 were obtained that not only bind human IFNAR 1 but also block IFN I signal.

The monoclonal antibodies of the present disclosure are prepared by standard monoclonal antibody preparation method. Mouse anti-human IFNAR1 monoclonal antibodies 10C2 and 10C9 were obtained by amplifying hybridoma cells in vivo or in vitro, in addition, the coding gene of the antibodies provided herein can also be cloned into eukaryotic expression vector by traditional molecular cloning method. The antibody was obtained by eukaryotic expression and purification. The specific procedures are as follows: The DNA molecule of SEQ ID NO. 1 is inserted into the eukaryotic expression vector (e.g. pCMV or pcDNA3.1) containing CMV promoter and selective puromycin gene to obtain a plasmid expressing heavy chain of the monoclonal antibody 10C2.

The DNA molecule of SEQ ID NO. 6 is inserted into the eukaryotic expression vector (e.g. pCMV or pcDNA3.1) containing CMV promoter and selective puromycin gene to obtain a plasmid expressing light chain of the monoclonal antibody 10C2.

Alternatively,

DNA molecule of SEQ ID NO. 11 is inserted into the eukaryotic expression vector (e.g. pCMV or pcDNA3.1) containing CMV promoter and selective puromycin gene to obtain a plasmid expressing heavy chain of the monoclonal antibody 10C2

DNA molecule of SEQ ID NO. 16 is inserted into the eukaryotic expression vector (e.g. pCMV or pcDNA3.1) containing CMV promoter and selective puromycin gene to obtain a plasmid expressing light chain of the monoclonal antibody 10C2.

The construction of recombinant cells includes the following steps: the plasmid expressing heavy chain of monoclonal antibody 10C2 and the plasmid expressing light chain of monoclonal antibody 10C2 are transfected into mammalian cells (e.g. CHO cells or HEK293T cells) using Lipofectamine 2000 (Invitrogen) in molar ratio of 1:1, and cell lines stably expressing monoclonal antibody 10C2 are obtained through resistance gene selection;

Alternatively, the construction of recombinant cells includes the following steps: the plasmid expressing heavy chain of monoclonal antibody 10C9 and the plasmid expressing light chain of monoclonal antibody 10C9 are transfected into mammalian cells (e.g. CHO cells or HEK293T cells) using Lipofectamine 2000 (Invitrogen) in molar ratio of 1:1, and cell lines stably expressing monoclonal antibody 10C9 are obtained through resistance gene selection.

The methods for in vitro expression and purification of monoclonal antibodies include the following steps: cultures of cell lines expressing IFNAR1 monoclonal antibody 10C2 and IFNAR1 monoclonal antibody 10C9 are expanded, respectively, and culture supernatant is collected; the supernatant can be filtered and concentrated, and purified monoclonal antibodies can be obtained by affinity chromatography with Nab Protein G Spin Column (GE). Eluted IgG can be checked by gel electrophoresis and high performance liquid chromatography to ensure purity. Concentration of the antibody is determined by BCA protein quantification method (Pierce). The monoclonal antibodies can be divided into aliquots and stored at −80° C.

The Twelfth Objective of the Present Disclosure is to Provide a Method for Inhibiting Biological Activity of a Type I Interferon on a Cell Expressing Interferon Alpha Receptor 1.

The present disclosure provides a method for inhibiting biological activity of a type I interferon on a cell expressing interferon alpha receptor 1, comprising contacting the cell with the monoclonal antibody of the present disclosure, or an antigen binding portion thereof, such that the biological activity of the type I interferon is inhibited.

The Thirteenth Objective of the Present Disclosure is to Provide a Method for Treating a Type I Interferon-Mediated Disease.

The method for treating a type I interferon-mediated disease comprises administering to the subject the monoclonal antibody of the present disclosure, or an antigen binding portion thereof, such that the type-I interferon mediated disease in the subject is treated.

In the above method, the type I interferon-mediated disease is selected from the group consisting of systemic lupus erythematosus, insulin dependent diabetes mellitus, inflammatory bowel disease, multiple sclerosis, psoriasis, autoimmune thyroiditis, rheumatoid arthritis and glomerulonephritis, HIV infection or AIDS, transplant rejection or graft versus host disease.

The antibodies (and immunoconjugates and bispecific molecules) of the present disclosure can be used to detect levels of IFNAR-1, or levels of cells that express IFNAR-1. This can be achieved, for example, by contacting a sample (such as an in vitro sample) and a control sample with the anti-IFNAR-1 antibody under conditions that allow for the formation of a complex between the antibody and IFNAR-1. Any complexes formed between the antibody and IFNAR-1 are detected and compared in the sample and the control. For example, standard detection methods, well-known in the art, such as ELISA and flow cytometric assays, can be performed using the compositions of the present disclosure.

The present disclosure further provides methods for detecting the presence of IFNAR-1 (e. g., human IFNAR-1 antigen) in a sample, or measuring the amount of IFNAR-1, comprising contacting the sample, and a control sample, with an antibody of the present disclosure, or an antigen binding portion thereof, which specifically binds to IFNAR-1, under conditions that allow for formation of a complex between the antibody or portion thereof and IFNAR-1. The formation of a complex is then detected, wherein a difference in complex formation between samples compared to the control sample is indicative of the presence of IFNAR-1 in the sample.

IFNAR-1 is part of the cellular receptor for Type I interferons, and Type I interferons are known to be immunoregulatory cytokines that are involved in, inter alia, T cell differentiation, antibody production and activity and survival of memory T cells. Moreover, increased expression of Type I interferons has been described in numerous autoimmune diseases, in HIV infection, in transplant rejection and in graft versus host disease (GVHD). Accordingly, the anti-IFNAR-1 antibodies (and immunoconjugates and bispecific molecules) of the present disclosure, which inhibit the functional activity of Type I interferons, can be used in a variety of clinical indications involving aberrant or undesired Type I interferon activity. The present disclosure, therefore, provides a method of inhibiting a Type I interferon-mediated disease or disorder, wherein the method comprises administering antibodies, or antigen-binding portion thereof, of the present disclosure (or immunconjugates or bispecific molecules of the present disclosure) such that the Type I interferon-mediated disease or disorder is treated.

Specific examples of autoimmune conditions in which the antibodies of the present disclosure can be used include, but are not limited to, the following: systemic lupus erythematosus (SLE), insulin dependent diabetes mellitus (DDM), inflammatory bowel disease (LBD) (including Crohn's Disease, Ulcerative Colitis and Celiac's Disease), multiple sclerosis (MS), psoriasis, autoimmune thyroiditis, rheumatoid arthritis (RA) and glomerulonephritis. Furthermore, the antibody compositions of the disclosure can be used for inhibiting or preventing transplant rejection or in the treatment of graft versus host disease (GVHD) or in the treatment of HIV infection/AIDS. High levels of IFNα have been observed in the serum of patients with systemic lupus erythematosus (SLE) (see e. g., Kim et al. (1987) Clin. Exp. Immunol. 70: 562-569). Moreover, administration of IFNα, for example in the treatment of cancer or viral infections, has been shown to induce SLE (Garcia-Porrua et al. (1998) Clin. Exp. Rheumatol. 16:107-108). Accordingly, in another embodiment, the anti-IFNAR-1 antibodies of the present disclosure can be used in the treatment of SLE by administering the antibody to a subject in need of treatment. The antibody can be used alone or in combination with other anti-SLE agents, such as non-steroidal anti-inflammatory drugs (NSAIDs), analgesics, corticosteroids (e. g., prednisone, hydrocortisone), immunosuppressants (such as cyclophosphamide, azathioprine, and methotrexate), antimalarials (such as hydroxychloroquine) and biologic drugs that inhibit the production of dsDNA antibodies (e. g., LJP 394).

IFNα also has been implicated in the pathology of Type I diabetes. For example, the presence of immunoreactive IFNα in pancreatic beta cells of Type I diabetes patients has been reported (Foulis et al. (1987) Lancet 2:1423-1427). Prolonged use of IFNa in anti-viral therapy also has been shown to induce Type I diabetes (Waguri et al. (1994) Diabetes Res. Clin. Pract. 23:33-36). Accordingly, in another embodiment, the anti-IFNAR-1 antibodies of the present disclosure can be used in the treatment of Type I diabetes by administering the antibody to a subject in need of treatment. The antibody can be used alone or in combination with other anti-diabetic agents, such as insulin.

Antibodies to IFNAR have been shown to be effective in an animal model of inflammatory bowel disease (see U.S. Patent Application 60/465,155). Thus, the anti-IFNAR-1 antibodies of the present disclosure can be used in the treatment of inflammatory bowel disease (IBD), including ulcerative colitis and Crohn's disease, by administering the antibody to a subject in need of treatment. The antibody can be used alone or in combination with other anti-IBD agents, such as drugs containing mesalamine (including sulfasalazine and other agents containing 5-aminosalicylic acid (5-ASA), such as olsalazine and balsalazide), non-steroidal anti-inflammatory drugs (NSAIDs), analgesics, corticosteroids (e.g., prednisone, hydrocortisone), TNF-inhibitors (including adilimumab (Humira®), etanercept (Enbrel®) and infliximab (Remicade)), immunosuppressants (such as 6-mercaptopurine, azathioprine and cyclosporine A), and antibiotics.

Treatment with IFNα has also been observed to induce autoimmune thyroiditis (Monzani et al. (2004) Clin. Exp. Med. 3:199-210; Prummel and Laurberg (2003) Thyroid 13:547-551). Accordingly, in another embodiment, the anti-IFNAR antibodies of the present disclosure can be used in the treatment of autoimmune thyroid disease, including autoimmune primary hypothyroidism, Graves' Disease, Hashimoto's thyroiditis and destructive thyroiditis with hypothyroidism, by administering the antibody to a subject in need of treatment. The antibody can be used alone or in combination with other agents or treatments, such as anti-thyroid drugs, radioactive iodine and subtotal thyroidectomy.

Increased levels of type I interferons, especially IFN-β, have been observed in the serum of patients with RA (see e. g., Hertzog et al. (1988) Clin. Immunol. Immunopath. 48: 192). Thus, in an embodiment, the anti-IFNAR-1 antibodies of the present disclosure can be used in the treatment of RA by administering the antibody to a subject in need of such treatment. The antibody can be used alone or in combination with one or more other anti-RA agent, such as a non-steroidal anti-inflammatory drug (NSAID), a COX-2 inhibitor, an analgesic, a corticosteroid (e. g., predinisone, hydrocortisone), gold, an immunosuppressant (e. g., methotrexate), a B-cell depletion agent (e.g., Rituxan™), a B-cell agonist (e. g., LymphoStat-B™) and an anti-TNF-α agent (e.g., EMBREL™, HUMIRA® and REMICADE™).

Administration of IFNα has been reported to exacerbate psoriasis. Accordingly, in another embodiment, the anti-IFNAR-1 antibodies of the present disclosure can be used in the treatment of psoriasis and psoriatic arthritis by administering the antibody to a subject in need of such treatment. The antibody can be used alone or in combination with one or more other anti-psoriasis treatments such as phototherapy, topical therapy (e. g., topical glucocorticoids), or systemic therapy (e. g., methotrexate, a synthetic retinoid, cyclosporine), an anti-TNF-α agent (e.g., EMBREL™, HUMIRA™ and REMICADE™), and a T-cell inhibitor (e.g., Raptiva™). High levels of IFNα also have been observed in the circulation of patients with HIV infection and its presence is a predictive marker of AIDS progression (DeStefano et al. (1982) J. Infec. Disease 146:451; Vadhan-Raj et al. (1986) Cancer Res. 46:417). Thus, in another embodiment, an anti-lFNAR-1 antibody of the present disclosure is used in the treatment of HIV infection or AIDS by administering the antibody to a subject in need of treatment. The antibody can be used alone or in combination with other anti-HIV agents, such as nucleoside reverse transcriptase inhibitors, non-nucleoside reverse transcriptase inhibitors, protease inhibitors and fusion inhibitors.

Antibodies to IFNAR-1 have been demonstrated to be effective in inhibiting allograft rejection and prolonging allograft survival (see e.g., Tovey et al. (1996) J. Leukoc. Biol. 59: 512-517; Benizri et al. (1998) J. Interferon Cytokine Res. 18:273-284). Accordingly, the anti-IFNAR-1 antibodies of the present disclosure also can be used in transplant recipients to inhibit allograft rejection and/or prolong allograft survival. The disclosure provides a method of inhibiting transplant rejection by administering an anti-IFNAR-1 antibody of the present disclosure to a transplant recipient in need of treatment. Examples of tissue transplants that can be treated include, but are not limited to, liver, lung, kidney, heart, small bowel, and pancreatic islet cells, as well as the treatment of graft versus host disease (GVHD). The antibody can be used alone or in combination with other agents for inhibiting transplant rejection, such as immunosuppressive agents (e. g., cyclosporine, azathioprine, methylprednisolone, prednisolone, prednisone, mycophenolate mofetil, sirilimus, rapamycin, tacrolimus), anti-infective agents (e. g., acyclovir, clotrimazole, ganciclovir, nystatin, trimethoprimsulfamethoxazole), diuretics (e. g., bumetanide, furosemide, metolazone) and ulcer medications (e. g., cimetidine, famotidine, lansoprazole, omeprazole, ranitidine, sucralfate).

The present disclosure relates to mouse monoclonal antibodies that bind to Interferon alpha receptor 1 (IFNAR-1) and that are capable of blocking the action of type I interferons, and immunoconjugates and bispecific molecules comprising such antibodies, and pharmaceutical compositions containing the antibodies, immunconjugates or bispecific molecules of the present disclosure. The present disclosure also relates to methods of using the antibodies to inhibit the binding of a type I interferon to IFNAR-1 on a cell expressing IFNAR-1, for example, in the treatment of immune mediated disorders, including autoimmune disorders, transplant rejection and Graft Versus Host Disease (GVHD), in a subject.

In order that the present disclosure may be more readily understood, certain terms are first defined. Additional definitions are set forth throughout the detailed description. The terms "Interferon alpha receptor-1," "IFNAR-1," and "IFNAR-1 antigen" are used interchangeably, and include variants, isoforms, species homologs of human IFNAR-1, and analogs having at least one common epitope with IFNAR-1. Accordingly, human antibodies of the present disclosure may, in certain cases, cross-react with IFNAR-1 from species other than human, or other proteins which are structurally related to human IFNAR-1 (e. g., human IFNAR-1 homologs). In other cases, the antibodies may be completely specific for human IFNAR-1 and not exhibit species or other types of cross-reactivity.

The complete cDNA sequence of human IFNAR-1 has the Genbank accession number NM_000629.

The term "type I interferon" as used herein is intended to refer to members of the type I interferon family of molecules that are ligands for IFNAR-1 (i.e., members of the type I interferon family of molecules that are capable of binding IFNAR-1). Examples of type I interferon ligands are interferon alpha 1, 2a, 2b, 4, 5, 6, 7, 8, 10, 14, 16, 17, 21, interferon beta and interferon omega.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the IFNAR-1 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CHI, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e. g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., IFNAR-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CHI domains; (ii) a F(ab')2 a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e. g., an isolated antibody that specifically binds IFNAR-1 is substantially free of antibodies that specifically bind antigens other than IFNAR-1). An isolated antibody that specifically binds IFNAR-1 may, however, have cross-reactivity to other antigens, such as IFNAR-1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Other features and advantages of the instant disclosure will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1 shows human type I interferon reporter cells. FIG. 1A shows the constructed human type I interferon reporter plasmid; FIG. 1B shows that the cell line stably transfected with type I interferon reporter plasmid expresses GFP after the cell line was stimulated with type I interferon.

FIG. 3 shows the nucleotide sequence (SEQ ID NO: 1) and amino acid sequence (SEQ ID NO: 2) of the heavy chain variable region of the IFNAR1 monoclonal antibody 10C2 (fused with signal peptide (SEQ ID NO: 47 for amino acid sequence and SEQ ID NO: 54 for nucleotide sequence) at N terminus). The CDR1 (SEQ ID NO: 3), CDR2 (SEQ ID NO: 4) and CDR3 (SEQ ID NO: 5) regions are delineated.

FIG. 4 shows the nucleotide sequence (SEQ ID NO: 6) and amino acid sequence (SEQ ID NO: 7) of the light chain variable region of the IFNAR1 monoclonal antibodyl0C2 (fused with signal peptide (SEQ ID NO: 48 for amino acid sequence and SEQ ID NO: 55 for nucleotide sequence) at N terminus). The CDR1 (SEQ ID NO: 8), CDR2 (SEQ ID NO: 9) and CDR3 (SEQ ID NO: 10) regions are delineated.

FIG. 7 shows the nucleotide sequence (SEQ ID NO: 11) and amino acid sequence (SEQ ID NO: 12) of the heavy chain variable region of the IFNAR1 monoclonal antibody 10C9 (fused with signal peptide (SEQ ID NO: 47 for amino acid sequence and SEQ ID NO: 54 for nucleotide sequence) at N terminus). The CDR1 (SEQ ID NO: 13), CDR2 (SEQ ID NO: 14) and CDR3 (SEQ ID NO: 15) regions are delineated.

FIG. 8 shows the nucleotide sequence (SEQ ID NO: 16) and amino acid sequence (SEQ ID NO: 17) of the light chain variable region of the IFNAR1 monoclonal antibodyl0C9 (fused with signal peptide (SEQ ID NO: 49 for amino acid sequence and SEQ ID NO: 56 for nucleotide sequence) at N terminus). The CDR1 (SEQ ID NO: 18), CDR2 (SEQ ID NO: 19) and CDR3 (SEQ ID NO: 20) regions are delineated.

DETAILED DESCRIPTION OF THE INVENTION

Figure 2:
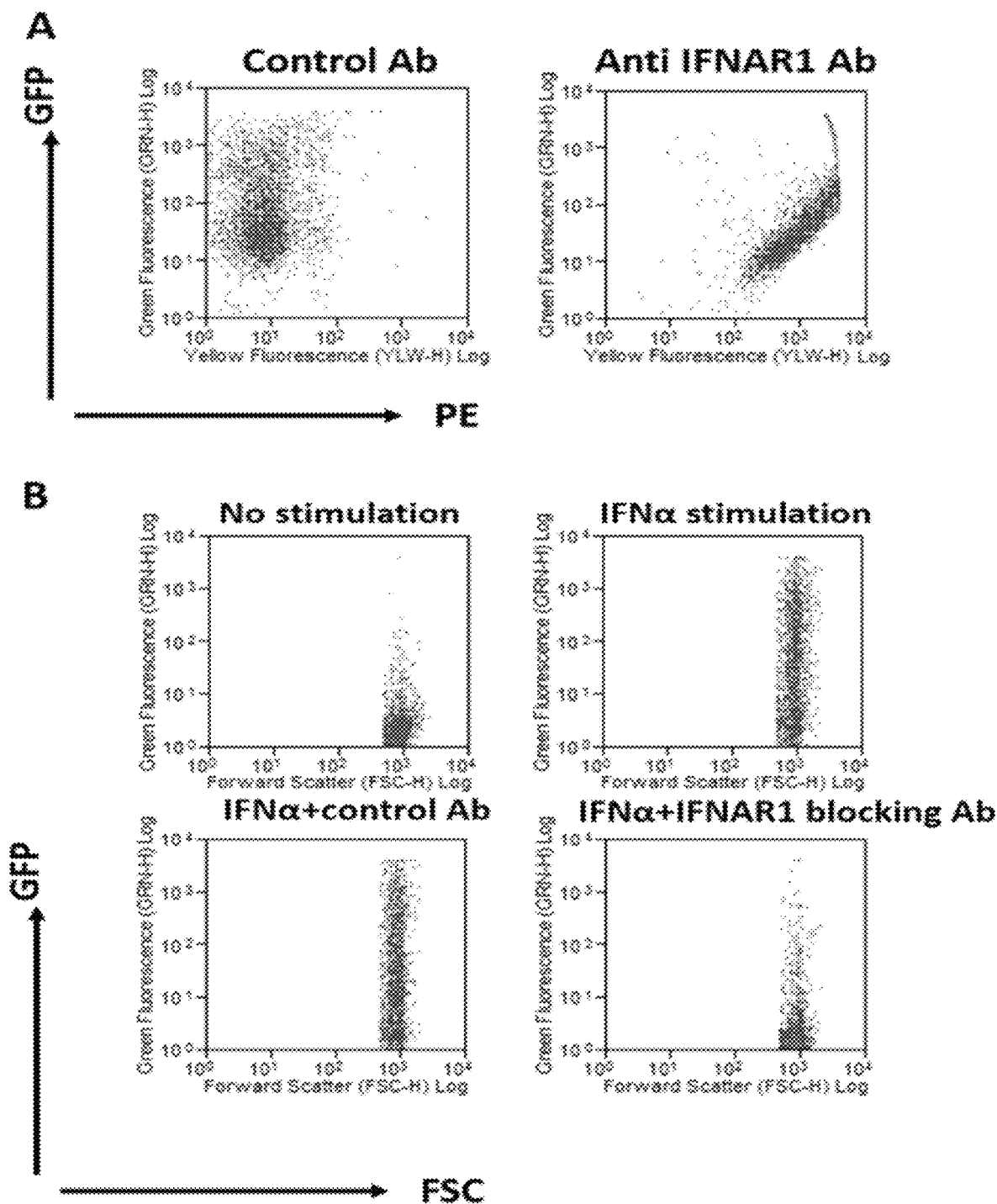
FIG. 2 shows the binding to IFNAR1 and screening of blocking antibody.

The methods used in the following examples are routine methods, unless otherwise specified.

The materials and reagents used in the following example can be obtained from commercial sources, unless otherwise specified.

Example 1: Generation of IFNAR1 Monoclonal Antibodies

I. Generation of type I interferon reporter cell line.

1. Primer Design

The genomic sequence of mouse interferon effector gene Mx2 (NCBI genebank: AB086958) was obtained according to the methods in the paper "Bürgi el al. Journal of Immunological Methods 381 (2012) 70-74). The effective sequence of Mx2 promoter was determined by the restriction sites (Nse I and Nhe I). The primers were designed according to the promoter sequence of Mx2:

```
F: CTAGCTAGCAAGTCTAAGGGCTCTGAGGACAGAC,    (SEQ ID NO: 25)

R: CCCAAGCTTCAAATGCCCTGCTGTACTTACCAGT.    (SEQ ID NO: 26)
```

2. PCR Amplification.

Using the mouse blood genomic cDNA as a template, PCR amplification was carried out using the above primers. The PCR amplification product was mouse Mx2 promoter fragment.

PCR reaction conditions: pre-denaturation at 98° C. for 2 minutes; denaturation at 98° C. for 30 seconds; annealing at 60° C. for 30 seconds; extension at 72° C. for 1 minute. A total of 30 cycles were run, and followed by an additional 10-minute denaturation.

3. Generation of pGL4.2 mouseMx2promoter-EGFP.

PCR amplification products and pGL4.2-EGFP (pGL4.2-EGFP is generated through replacing eGFP with luc2 gene from pGL4(luc2)) were digested by restriction enzyme KpnI and NheI. pGL4.2 mouseMx2promoter-EGFP was generated after ligation. FIG. 1A shows the structure of plasmid pGL4.2 mouseMx2promoter-EGFP.

4. Generation of type I interferon reporter cell line.

The plasmid pGL4.2 mouseMx2promoter-EGFP was transfected into HEK293T cells (ATCC, cat.no.: ATCC® CRL-3216™) using Lipofectamine 2000 (Invitrogen). The stable transfected cell line (type I interferon reporter cell line) was generated after puromycin selection.

5. Functional verification of type I interferon reporter cell line.

The stable transfected cell line generated by step 4 was stimulated with 100 μL 5 ng/mL human IFNα2b (Cedarlane, cat.no. CL06-04E-100UG). After 24 hours, the cells was harvested and the expression of GFP was detected by flow cytometry.

As shown in FIG. 1B: type I interferon reporter cell line did not express GFP without type I interferon stimulation, but it expressed GFP after type I interferon stimulation. The signal of GFP can be detected by flow cytometry. Thus the cell line generated by step 4 can be used as type I interferon reporter cell line and for screening IFNAR1 blocking antibodies.

II. Generation of human type I interferon receptor IFNAR1 monoclonal antibodies.

1. Preparation of human IFNAR1 antigen.

(1) The primers were designed according to human IFNAR1 sequence:

```
IFNAR1-F:
                                          (SEQ ID NO: 27)
CTAGCTAGCTCTAGAGCCACCATGATGGTCGTCCTCCTGGGC,

IFNAR1-R:
                                          (SEQ ID NO: 28)
GGGTCCGGAACCTCCTCCTCCCACAGCATAAATGACAAACGGGAGA.
```

(2) Using human PBMCs cDNA as a template, PCR amplification was carried out using the above primers to obtain PCR amplification products which were extracellular domains and transmembrane domains of human IFNAR1.

The PCR reaction conditions were: pre-denaturation at 98° C. for 2 minutes; denaturation at 98° C. for 30 seconds; annealing at 60° C. for 30 seconds; extension at 72° C. for 1 minute. A total of 30 cycles were run, and followed by an additional 10-minute extension.

(3) PCR amplification products and pEGFP were digested by restriction enzyme Nhe I and Bspe I. pEGFP-humanIFNAR1EC was generated after ligation.

GFP gene was fused with IFNAR1 extracellular and transmembrane domains in the pEGFP-humanIFNAR1EC plasmid. GFP signal can be detected when IFNAR1 was expressed.

(4) The plasmid pEGFP-humanIFNAR1EC was transfected into mouse L cells (ATCC, cat.no.: ATCC® CRL-2648™) using Lipofectamine 2000 (Invitrogen). After 48 hours, the mouse L cells transfected with IFNAR1 extracellular domain were obtained. The transfection efficiency was determined by analyzing the GFP expression in mouse L cells transfected with IFNAR1 extracellular domain.

2. Immunization of BALB/c mouse.

The mouse L cells transfected with IFNAR1 extracellular domain were used as immunogen. 5000,000 mouse L cells transfected with IFNAR1 extracellular domain were mixed with 20 μg CpG1826 (TAKARA) to get 0.5 mL suspension. 6 weeks BALB/c mice were immunized through intraperitoneal injection. Immunization were conducted once a month, for a total of 3 times. At last, the mice were boosted using the same methods. Hybridoma fusion was prepared after 4 days.

3. Generation of cell line stably expressing human IFNAR1 extracellular domain.

The plasmid pEGFP-humanIFNAR1EC was transfected into HEK293T using Lipofectamine 2000. The stably transfected cell line were generated by pyromycin selection. The cell line stably expressed IFNAR1 extracellular and transmembrane domain and used for the following antibody screening test.

4. Hybridoma fusion

The immunized mice were sacrificed, and the spleen cells were taken out. Mice spleen cells were mixed with mouse myeloma cell line SP2/0 (ATCC, CRL1581) by 50% PEG (sigma) at a ratio 1:3.

The fused cells were resuspended with 60 mL RPMI culture medium contain 1×HAT(Cellgro,cat.no:15-041-CV) and 10% FBS. 1-2 drops were added into 96-well cell culture plates. Then the hybridoma cells were cultured in 5% $CO_2$ incubator at 37° C. Half of the medium were changed after 3-4 days. The antibodies were screened after 10 days.

5. Screening human IFNAR1 monoclonal antibodies.

The day before screening, 100 μL supernatant was aspirated from 96-well cell culture plate into a 96-well U bottom plate. 100 μL fresh 1×HAT RPMI medium was added to the original well for continued culture. HEK293T cells stably expressing IFNAR1 were harvested and were subsequently added to a 96-well U-bottom plate at a density of 10,000 cells/200 μL/well. After centrifugation at 2200 rpm for 3 min, the supernatant was discarded and the cell pellet was collected and re-suspended with 100 μL hybridoma supernatant at 4° C. for 30 min. After the incubation, the cells were centrifuged and re-suspended with 200 μL of FACS buffer (contain 2% FBS and 2 mM EDTA in PBS), before next centrifugation and re-suspension. PE-labeled goat anti-mouse IgG antibody (Biolegend) diluted in FACS buffer at 1:400 was added to each well. The cells were re-suspended and incubated at 4° C. for 30 min in the dark. After the incubation, the plate was centrifuged, the supernatant was discarded, and the cells were washed once as described above and re-suspended by adding 200 μL FACS buffer. Finally, the re-suspended cells were analyzed using a flow cytometer Guava (Millipore) for cellular GFP and PE signal. The results are shown in FIG. 2A. It was shown that GFP and PE double positive wells are binding human IFNAR1 positive well, as the GFP-positive cells in the plot were shifted to the right.

The culture supernatants of the positive well were used to do the next blocking functional experiment. The specific steps are as follows: first of all, the human type I interferon reporter cells were added to a 96-well plate (30,000 cells/well) and cultured for 24 hours. The supernatant in the cell culture was removed and the cells were treated with 100 μL hybridoma supernatant. The cells were then incubated at 37° C. for 1 h, before treating with 10 ng/mL human IFNα2b in 100 μL DMEM (Hyclone SH30022.01) with 10% FBS. The treated cells were further cultured for 24 hours, before the cells were analyzed by flow cytometry to determine the blockade effect of the antibodies to the type I IFN-induced GFP-expression in the reporter cells. Samples with low GFP expression were IFNAR1 blocking antibodies (FIG. 2B). According to the above steps, 10C2 and 10C9 were selected as the monoclonal hybridoma cell lines stably secreting IFNAR1 monoclonal antibodies, which not only bind human IFNAR1, but also block its signal. They were named as hybridoma cell line 10C2 and hybridoma cell line 10C9. The antibody secreted by hybridoma cell line 10C2 was anti-human IFNAR1 monoclonal antibody 10C2, the antibody secreted by hybridoma cell line 10C9 was anti-human IFNAR1 monoclonal antibody 10C9.

The proposed taxonomic name of hybridoma cell line 10C2 was mouse hybridoma cell line, the hybridoma cell line was deposited at China General Microbiological Culture Collection center (CGMCC, Institute of Microbiology Chinese Academy of Sciences, No. 1 West Beichen Road, Chaoyang District, Beijing 100101, China). The deposit date is May 31, 2016. The deposit no. is CGMCC No. 12542.

The proposed taxonomic name of hybridoma cell line 10C9 was mouse hybridoma cell line, the hybridoma cell line was deposited at China General Microbiological Culture Collection center (CGMCC, Institute of Microbiology Chinese Academy of Sciences, No. 1 West Beichen Road, Chaoyang District, Beijing 100101, China). The deposit date is May 31, 2016. The deposit no. is CGMCC No. 12543.

III. Sequence of mouse anti-human IFNAR1 monoclonal antibody 10C2 and 10C9

1. RNA extraction

Hybridoma cell lines 10C2 and 10C9 were lysed using Trizol (Invitrogen) to extract the RNA of the hybridoma cell lines. The specific steps of RNA Extraction were as follows:

200 μL Chloroform were added to every 1mL Trizol, and vortexed thoroughly before 10-min settlement. After centrifugation at 13000 rpm/4° C. for 15 min, 400 μL supernatant was pipetted into 400 μL pre-cooled isopropanol, before mixing and placing at −20° C. overnight. After centrifugation at 13000 rpm/4° C. for 15 min, the supernatant was removed and 70% ethanol was added. The mixture was centrifuged at 13000 rpm/4° C. for 10 min, the supernatant was removed and 70% ethanol was added. The supernatant was removed and 401 μL water was added into the pellet to dissolve and obtain the RNA solution.

2. cDNA Preparation

161 μL RNA solution as obtained were aspirated and 1 μL 100 nM Oligo dT (Invitrogen) was added. After reaction at 70° C. for 5 min, the tube was placed onto the ice immediately. 1 μL RNA polymerase inhibitor (Takara), 1 μL 10 mM dNTP(Takara), 1 μL MLV reverse transcriptase and 5× buffer(Promega) were added. The mixture were allowed for reaction at 42° C. for 60 min, and treatment at 80° C. for 10 min.

3. PCR amplification and sequencing

The cDNA as obtained in step 2 was used as a template, PCR amplification was carried out using a heavy chain primer pair (including heavy chain primer F and heavy chain primer R) and a light chain primer pair (including light chain primer F and light chain primer R), see below primer sequences:

```
Heavy chain primer F:
                                        (SEQ ID NO: 29)
CTAGCTAGCTCTAGAGCCACCATGATGGTCGTCCTCCTGGGC, Heavy chain primer R:
                                        (SEQ ID NO: 30)
CTTGACCAGGCATCCTAGAGTCA, Light chain primer F:
                                        (SEQ ID NO: 31)
GAYATTGTGMTSACMCARWCTMCA, Light chain primer R:
                                        (SEQ ID NO: 32)
GGATACAGTTGGTGCAGCATC.
```

PCR reaction conditions: pre-denaturation at 98° C. for 2 minutes; denaturation at 98° C. for 30 seconds; annealing at 54° C. for 30 seconds; extension at 72° C. for 1 minute. A total of 35 cycles were run, followed by an additional 10-min extension.

The sequencing result showed that:

The nucleotide sequences and amino acid sequences of the heavy chain variable region of IFNAR1 monoclonal antibody 10C2 are shown in FIG. 3. The nucleotide sequences of the heavy chain variable region of IFNAR1 monoclonal antibody 10C2 are SEQ No.1. The amino acid sequences of the heavy chain variable region of IFNAR1 monoclonal antibody 10C2 are SEQ No. 2. The 26th-33rd amino acid residues (SEQ No. 3) of the heavy chain variable region of IFNAR1 monoclonal antibody 10C2 was named as 10C2 heavy chain CDR1. The 51st-58th amino acid residues (SEQ No. 4) of the heavy chain variable region of IFNAR1 monoclonal antibody 10C2 was named as 10C2 heavy chain CDR2. The 97th-112th amino acid residues (SEQ No. 5) of the heavy chain variable region of IFNAR1 monoclonal antibody 10C2 was named as 10C2 heavy chain CDR3.

The nucleotide sequences and amino acid sequences of the light chain variable region of IFNAR1 monoclonal antibody 10C2 are shown in FIG. 4. The nucleotide sequences of the light chain variable region of IFNAR1 monoclonal antibody 10C2 are SEQ No. 6. The amino acid sequences of the light chain variable region of IFNAR1 monoclonal antibody 10C2 are SEQ No. 7. The 27th-32nd amino acid residues (SEQ No. 8) of the light chain variable region of IFNAR1 monoclonal antibody 10C2 was named as 10C2 light chain CDR1. The 50th-52th amino acid residues (SEQ No. 9) of the light chain variable region of IFNAR1 monoclonal antibody 10C2 was named as 10C2 light chain CDR2. The 89th-94th amino acid residues (SEQ No. 10) of the light chain variable region of IFNAR1 monoclonal antibody 10C2 was named as 10C2 light chain CDR3.

The nucleotide sequences and amino acid sequences of the heavy chain variable region of IFNAR1 monoclonal antibody 10C9 are shown in FIG. 7. The nucleotide sequences of the heavy chain variable region of IFNAR1 monoclonal antibody 10C9 are SEQ No. 11. The amino acid sequences of the heavy chain variable region of IFNAR1 monoclonal antibody 10C9 are SEQ No. 12. The 26th-33rd amino acid residues (SEQ No. 13) of the heavy chain variable region of IFNAR1 monoclonal antibody 10C9 was named as 10C9 heavy chain CDR1. The 51st-58th amino acid residues (SEQ No. 14) of the heavy chain variable region of IFNAR1 monoclonal antibody 10C9 was named as 10C9 heavy chain CDR2. The 97th-112th amino acid residues (SEQ No. 15) of the heavy chain variable region of IFNAR1 monoclonal antibody 10C9 was named as 10C9 heavy chain CDR3.

The nucleotide sequences and amino acid sequences of the light chain variable region of IFNAR1 monoclonal antibody 10C9 are shown in FIG. 8. The nucleotide sequences of the light chain variable region of IFNAR1 monoclonal antibody 10C9 are SEQ No. 16. The amino acid sequences of the light chain variable region of IFNAR1 monoclonal antibody 10C9 are SEQ No. 17. The 27th-32nd amino acid residues (SEQ No. 18) of the light chain variable region of IFNAR1 monoclonal antibody 10C9 was named as 10C9 light chain CDR1. The 50th-52th amino acid residues (SEQ No. 19) of the light chain variable region of IFNAR1 monoclonal antibody 10C9 was named as 10C9 light chain CDR2. The 89th-96th amino acid residues (SEQ No. 20) of the light chain variable region of IFNAR1 monoclonal antibody 10C9 was named as 10C9 light chain CDR3.

4. Sequence Analysis of Antibodies

The nucleic acid fragments of the antibodies 10C2 and 10C9 were analyzed using the igblast tool (http://www.ncbi.nlm.nih.gov/igblast/) and the results were as follows.

Figure 5:
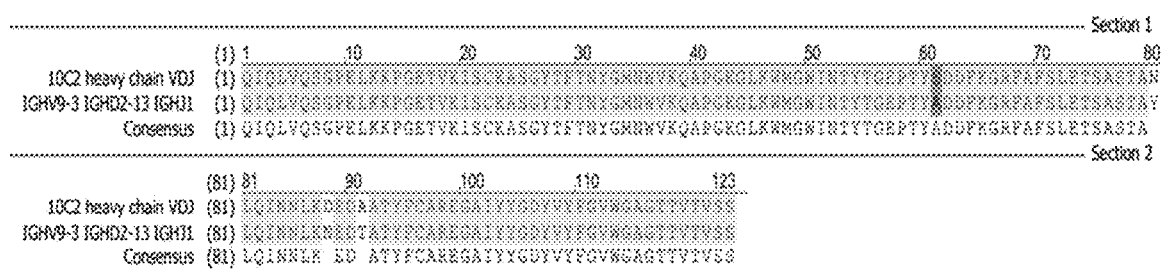
FIG. 5 shows the alignment of the amino acid sequence (SEQ ID NO: 2) of the heavy chain variable region of 10C2 with the mouse germline V region amino acid sequence (SEQ ID NO: 21). The composition of the heavy chain variable region of IFNAR1 monoclonal antibodyl0C2: V gene is IGHV9-3, D gene is GHD2-13, J gene is IGHJ1. Alignment of amino acid sequence of the heavy chain variable region of 10C2 and its amino acid of original VDJ gene is shown as consensus sequence (SEQ ID NO: 53).
Figure 6:
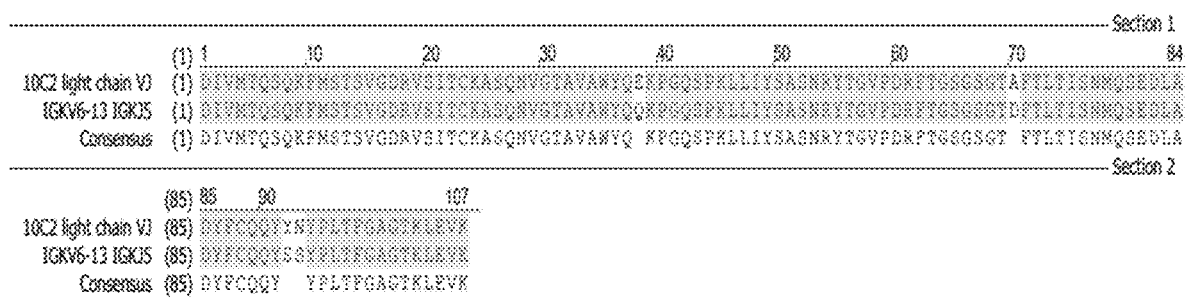
FIG. 6 shows the alignment of the amino acid sequence of the light chain variable region of 10C2 (SEQ ID NO: 7) with the mouse germline V region amino acid sequence (SEQ ID NO: 22). The composition of the light chain variable region of IFNAR1 monoclonal antibody 10C2: V gene is IGKV6-13, J gene is IGKJ5. Alignment of amino acid sequence of the light chain variable region of 10C2 and its amino acid of original VDJ gene is shown as consensus sequence (SEQ ID NO: 50).

The V gene, D gene and J gene of the heavy chain encoding gene of antibody 10C2 correspond to mouse IGHV9-3 gene, IGHD2-13 gene and IGHJ1 gene, respectively. The alignment results between the amino acid sequence of the heavy chain variable region of antibody 10C2 (SEQ ID NO: 2) and the amino acid sequence of mouse V region (SEQ ID NO: 21) are shown in FIG. 5. The V gene and J gene of the light chain encoding gene of antibody 10C2 correspond to mouse IGKV6-13 gene and IGKJ5 gene, respectively. The alignment results between the amino acid sequence of the light chain variable region of antibody 10C2 (SEQ ID NO: 7) and the amino acid sequence of mouse V region (SEQ ID NO: 22) are shown in FIG. 6.

Figure 9:
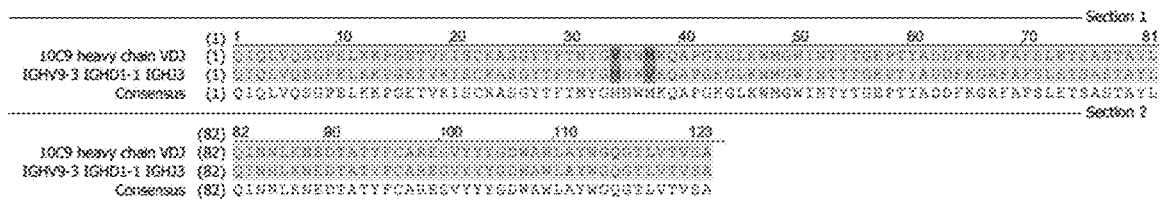
FIG. 9 shows the alignment of the amino acid sequence (SEQ ID NO: 12) of the heavy chain variable region of 10C9 with the mouse germline V region amino acid sequence (SEQ ID NO: 23). The composition of the heavy chain variable region of IFNAR1 monoclonal antibodyl0C9: V gene is IGHV9-3, D gene is IGHD1-1, J gene is IGHJ3. Alignment of amino acid sequence of the heavy chain variable region of 10C9 and the amino acid of original VDJ gene is shown as consensus sequence (SEQ ID NO: 51).
Figure 10:
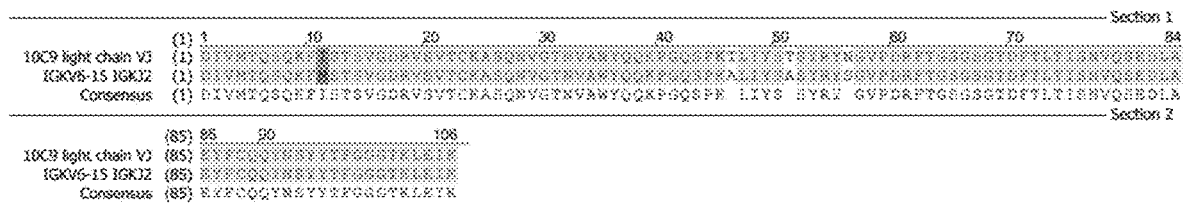
FIG. 10 shows the alignment of the amino acid sequence of the light chain variable region (SEQ ID NO: 17) of 10C9 with the mouse germline V region amino acid sequence (SEQ ID NO: 24). The composition of the light chain variable region of IFNAR1 human monoclonal antibody 10C2: V gene is IGKV6-15, J gene is IGKJ2. Alignment of amino acid sequence of the light chain variable region of 10C9 and the amino acid of original VJ gene is shown as consensus sequence (SEQ ID NO: 52).

The V gene, D gene and J gene of the heavy chain encoding gene of antibody 10C9 correspond to mouse IGHV9-3 gene, IGHD1-1 gene and IGHJ3 gene, respectively. The alignment results between the amino acid sequence of the heavy chain variable region of antibody 10C9 (SEQ ID NO: 12) and the amino acid sequence of mouse V region (SEQ ID NO: 23) are shown in FIG. 9. The V gene and J gene of the light chain encoding gene of antibody 10C9 correspond to mouse IGKV6-15 gene and IGKJ2 gene, respectively. The alignment results between the amino acid sequence of the light chain variable region of antibody 10C9 (SEQ ID NO: 17) and the amino acid sequence of mouse V region (SEQ ID NO: 24) are shown in FIG. 10.

Example 2: IFNAR1 Monoclonal Antibodies Bind to the Human IFN-I Receptor IFNAR1

1. The HEK293T cells stably expressing human IFN-I receptor IFNAR1 as obtained from step 3 of Example 1 were diluted with 2 mM EDTA in PBS (1L PBS contain KH2PO4 0.27 g, Na2HPO4 1.42 g, NaCl 8 g. KCl 0.2 g, pH=7.2-7.4) to make single cell suspension.

2. The above cells were subsequently added to a 96-well U-bottom plate at a density of 10,000 cells/200 L/well. After centrifugation at 2200 rpm for 3 min, the supernatant was discarded and the cell pellet was collected and re-suspended.

3. The test antibody (10C2 or 10C9 or an isotype antibody) was diluted with FACS buffer to a concentration of 5 μg/ml, and incubated with the re-suspended cell pellet at 4° C. for 30 min.

4. After the incubation, the cells were centrifuged and re-suspended with 200 μL of FACS buffer, before next centrifugation and re-suspension.

5. PE-labeled goat anti-mouse IgG antibody (Biolegend) diluted in FACS buffer at 1:400 was added to each well. The cells were re-suspended and incubated at 4° C. for 30 min in the dark. After the incubation, the plate was centrifuged, the supernatant was discarded, and the cells were washed once as described above and re-suspended by adding 200 μL FACS buffer. Finally, the re-suspended cells were analyzed using a flow cytometer Guava (Millipore) for cellular PE signal.

Figure 11:
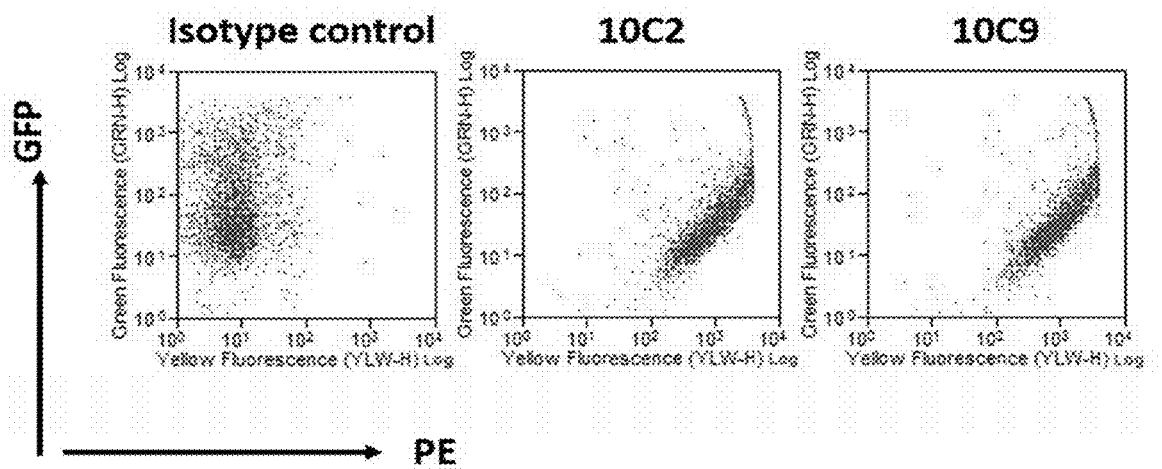
FIG. 11 shows binding of IFNAR1 monoclonal antibodies10C2 and 10C9 with IFNAR1.

The results are shown in FIG. 11. As IFNAR1 and GFP were expressed as a fusion, cells that express high level of GFP expressed higher IFNAR1. Thus, cells that expressed high level of GFP bound to much more anti-human IFNAR1 antibodies and bound to much more PE-labeled goat anti-mouse IgG antibody. Thus these cells had much higher PE signal. As shown in FIG. 1: both mouse anti-human IFNAR1 monoclonal antibody 10C2 and 10C9 bound to human IFNAR1.

Example 3: IFNAR1 Monoclonal Antibodies Bind to the SDZ and SD3 Domain of Human IFN-I Receptor IFNAR1

I. Construction of Expression Plasmids for Human IFNAR1 Truncations Lacking Extracellular SD1, SD2 and SD3.

1. Primer Design

The primers were designed according to the sequence of human IFNAR1 and expressing plasmid:

```
F:
        (SEQ ID NO: 33, located in the CMV promoter of
                              IFNAR1 expressing plasmid)
ATTGACGCAAATGGGCGGTA, 1F:
                                           (SEQ ID NO: 34)
CAGGTGGAAAAAATCTAAAACAGATTGGTCCTCCAGAAGTACATT, 1R:
                                           (SEQ ID NO: 35)
ACTTCTGGAGGACCAATCTGTTTTAGATTTTTTCCACCTGCGGC, 2F:
                                           (SEQ ID NO: 36)
TTACACCATTTCGCAAAGCTGAACTACCTCCACCAGAAAATATA, 2R:
                                           (SEQ ID NO: 37)
TTTTCTGGTGGAGGTAGTTCAGCTTTGCGAAATGGTGTAAATGAG, 3F:
                                           (SEQ ID NO: 38)
CAGTTGAAAATGAACTACCTTTCCTACTTCCTCCACTCTTTAACA, 3R:
                                           (SEQ ID NO: 39)
ACTGGAGGAAGTAGGAAAGCAGGTAGTTCATTTTCAACTGTGGTC, R:
                                           (SEQ ID NO: 40)
GGGTCCGGAACCTCCTCCTCCCACAGCATAAATGACAAACGGGAGA.
```

2. Construction of expression plasmids for human IFNAR1 truncations lacking extracellular SD1, SD2 and SD3.

(1) Construction of expression plasmid of human IFNAR1 truncations lacking extracellular SD1.

(A) the pEGFP-humanIFNAR1EC plasmid of Example 1 was used as a template, to obtain the PCR products of the first round using F/1R and 1F/R as primers for the first round PCR.

PCR reaction conditions: pre-denaturation at 98° C. for 2 minutes; denaturation at 98° C. for 30 seconds; annealing at 58° C. for 30 seconds; extension at 72° C. for 2 minute. A total of 30 cycles were run, followed by an additional 10-min denaturation.

(B) the PCR products of the first round PCR were harvested and were used as the template for the second round PCR, using F and R as primers to get the second round PCR products.

PCR reaction conditions: pre-denaturation at 98° C. for 2 minutes; denaturation at 98° C. for 30 seconds; annealing at 58° C. for 30 seconds; extension at 72° C. for 2 minute. A total of 30 cycles were run, followed by an additional 10-min denaturation.

(C) the PCR products of the second round PCR were harvested. The second round PCR products and pEGFP-humanIFNAR1EC were digested by restriction enzyme EcoRI and BspeI. The products were recovered and ligated to obtain the expressing plasmid for SD1-truncated IFNAR1.

The expressing plasmid for SD1-truncated IFNAR1 is a vector obtained by replacing the gene encoding for human IFNAR1 extracellular SD1 domain (i.e. the encoding gene for the $32^{nd}$-$126^{th}$ amino acid of IFNAR1 amino acid sequence) with the fragment flanked by EcoRI and Bspe I restriction sites in the pEGFP-humanIFNAR1EC plasmid, and keeping the other sequences unchanged.

(2) Construction of expression plasmid of human IFNAR1 truncations lacking extracellular SD2.

(A) the pEGFP-humanIFNAR1 EC plasmid of Example I was used as a template, to obtain the PCR products of the first round using F and 2R, and 2F and R as primers for the first round PCR.

PCR reaction conditions: pre-denaturation at 98° C. for 2 minutes; denaturation at 98° C. for 30 seconds; annealing at 58° C. for 30 seconds; extension at 72° C. for 2 minute. A total of 30 cycles were run, followed by an additional 10-min denaturation.

(B) the PCR products of the first round PCR were harvested and were used as the template for the second round PCR, using F and R as primers to get the second round PCR products.

PCR reaction conditions: pre-denaturation at 98° C. for 2 minutes; denaturation at 98° C. for 30 seconds; annealing at 58° C. for 30 seconds; extension at 72° C. for 2 minutes. A total of 30 cycles were run, followed by an additional 10-min denaturation.

(C) the PCR products of the second round PCR were harvested. The second round PCR products and pEGFP-humanIFNAR1EC were digested by restriction enzyme EcoRI and BspeI. The products were recovered and ligated to obtain the expressing plasmid for SD2-truncated IFNAR1.

The expressing plasmid for SD2-truncated IFNAR1 is a vector obtained by replacing the gene encoding for human IFNAR1 extracellular SD2 domain (i.e. the encoding gene for the $127^{th}$-$227^{th}$ amino acid of IFNAR1 amino acid sequence) with the fragment flanked by EcoRI and Bspe I restriction sites in the pEGFP-humanIFNAR1EC plasmid, and keeping the other sequences unchanged.

(3) Construction of expression plasmid of human IFNAR1 truncation lacking extracellular SD3.

(A) the pEGFP-humanIFNAR1 EC plasmid of Example I was used as a template, to obtain the PCR products of the first round using F and 3R, and 3F and R as primers for the first round PCR.

PCR reaction conditions: pre-denaturation at 98° C. for 2 minutes; denaturation at 98° C. for 30 seconds; annealing at 58° C. for 30 seconds; extension at 72° C. for 2 minute. A total of 30 cycles were run, followed by an additional 10-min denaturation, and the template was the IFNAR1 expressing plasmid as described above.

(B) the PCR products of the first round PCR were harvested and were used as the template for the second round PCR, using F and R as primers to get the second round PCR products.

PCR reaction conditions: pre-denaturation at 98° C. for 2 minutes; denaturation at 98° C. for 30 seconds; annealing at 58° C. for 30 seconds; extension at 72° C. for 2 minutes. A total of 30 cycles were run, followed by an additional 10-min denaturation.

(C) the PCR products of the second round PCR were harvested. The second round PCR products and pEGFP-humanIFNAR1EC were digested by restriction enzyme EcoRI and BspeI. The products were recovered and ligated to obtain the expressing plasmid for SD3-truncated IFNAR1.

The expressing plasmid for SD3-truncated IFNAR1 is a vector obtained by replacing the gene encoding for human IFNAR1 extracellular SD3 domain (i.e. the encoding gene for the $231^{st}$-$329^{th}$ amino acid of IFNAR1 amino acid sequence) with the fragment flanked by EcoRI and Bspe I restriction sites in the pEGFP-humanIFNAR1EC plasmid, and keeping the other sequences unchanged.

3. Construction of HEK 293 cells expressing human IFNAR1 truncations lacking extracellular SD1, SD2 and SD3.

Plasmids expressing wild type IFNAR1 (pEGFP-humanIFNAR1EC) and expressing human IFNAR1 truncations lacking extracellular SD1, SD2 or SD3 were transfected into HEK293T cells using Lipofectamine 2000 (Invitrogen) respectively. 24 hours later, the cells were treated with 2 mM EDTA in PBS and harvested single cell suspension. HEK293T expressing human IFNAR1 (R1-WT), HEK293T expressing human IFNAR1 truncation lacking extracellular SD1(RI-Δ1), HEK293T expressing human IFNAR1 truncation lacking extracellular SD1(R1-Δ2) and HEK293T expressing human IFNAR1 truncation lacking extracellular SD1(R1-Δ3) were separately generated II the Binding of IFNAR1 Monoclonal Antibody 10C2 and 10C9 with Each Human IFNAR1 Truncation.

According to methods of Example 2, the binding of IFNAR1 monoclonal antibody 10C2 and 10C9 were detected with HEK293T cells expressing human interferon type I receptor IFNAR1 (R1-WT), HEK293T cells expressing human interferon type I receptor IFNAR1-SD1 truncation (R1-Δ 1), HEK293T cells expressing human interferon type I receptor IFNAR1-SD1 truncation (RI-Δ2), and HEK293T cells expressing human interferon type I receptor IFNAR1-SD1 truncation (R1-Δ3).

Figure 12:
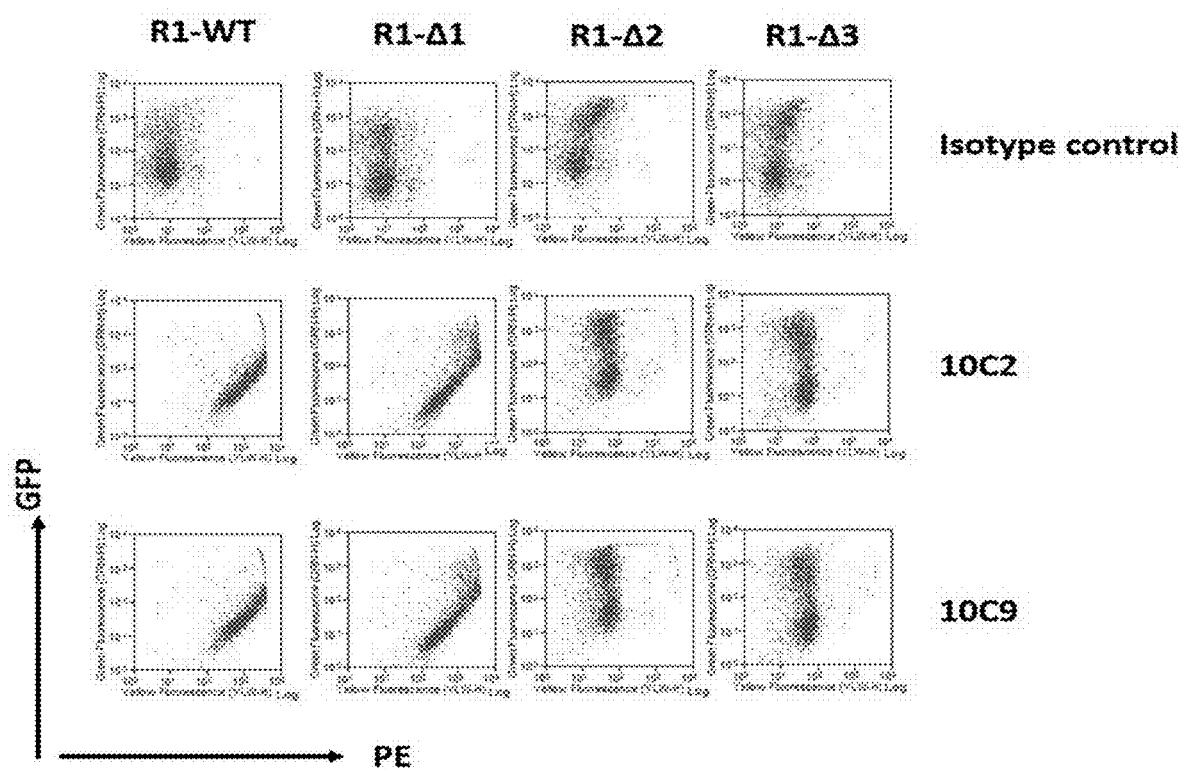
FIG. 12 shows binding of SD2 and/or SD3 domain of IFNAR1 monoclonal antibodies10C2 and 10C9 with IFNAR1.

As shown in FIG. 12, neither of IFNAR1 monoclonal antibodies 10C2 and 10C9 bound to HEK293T cells expressing human interferon type I receptor IFNAR1-SD1 truncation (R-Δ11), but both bound to HEK293T cells expressing human interferon type I receptor IFNAR1-SD1 truncation (R1-Δ2), and HEK293T cells expressing human interferon type I receptor IFNAR1-SD1 truncation (R1-Δ3). These results indicated that the IFNAR1 monoclonal antibodies can specifically bind SD2 and/or SD3 domains of human IFNAR1.

Example 4. Effects of Anti-Human IFNAR1 Monoclonal Antibodies on Blocking the Biological Activity of IFNα2b Type I interferon reporter cell line of Example I was used as a tool to analyze the efficiency of IFNAR1 monoclonal antibody 10C2 and 10C9 to block IFN-I. The specific steps are as follows:

1. The human type I interferon reporter cells were added to a 96-well plate at 30,000 cells/200 μL/well, and cultured for 24 h.
2. Serial-diluted antibodies (at a concentration of 20 μg/ml, 105 μg/ml, 5 μg/ml, 2.5 μg/ml, 1.25 μg/ml, 0.625 μg/ml, 0.313 μg/ml, 0.156 μg/ml, 0.078 μg/ml, 0 μg/ml) were added to DMEM culture medium supplemented with 10% FBS.
3. The supernatant in the cell culture was removed, and 100 μl of the DMEM culture medium containing the serial-diluted antibodies were added, followed by incubation at 37° C. for 1 h.
4. 100 uL DMEM medium containing 10 ng/mL human IFNα2b (Cedarlane, cat.no. CL106-04E-100UG) was added to the wells for stimulation and incubated at 37° C., 5% CO$_2$ for 24 hours.
5. The GFP signal was analyzed by flow cytometry to determine the effect of the antibodies to block the biological activity of the Type I interferon signaling.

Figure 13:
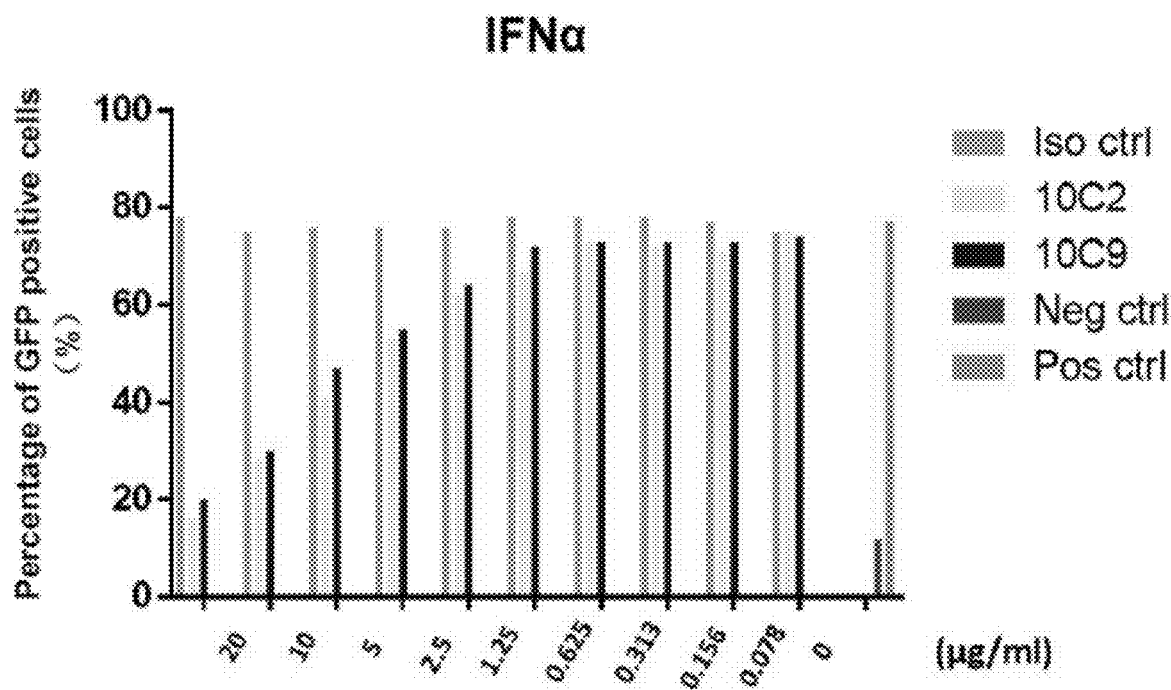
FIG. 13 shows that IFNAR1 monoclonal antibodies10C2 and 10C9 inhibit the biological activity of IFNα2b on interferon signal reporter cells.

The results are shown in FIG. 13. "Iso ctrl" represents istotype control (mIgG2a, Biolegend), "Neg ctrl" represents control sample without IFNα2b stimulation, "Pos ctrl" represents control sample only with IFNα2b stimulation. As the Figure shows, GFP expression level decreased after treating with serial-diluted IFNAR1 monoclonal antibody 10C2 and 10C9. As the concentration increased, the GFP expression level gradually reduced, indicating that both IFNAR1 monoclonal antibodies 10C2 and 10C9 can effectively block IFNα2b signaling, suggesting that the IFNAR1 monoclonal antibodies can block the biological activity of IFNα2b.

Example 5. Effects of IFNAR1 Monoclonal Antibodies on Blocking the Stimulation of Type I Interferon on Human Peripheral Blood Mononuclear Cells 1. Different concentrations (1 μg/ml, 10 μg/ml) of IFANR1 monoclonal antibody 10C2 and 10C9 were added to RPMI 1640 (Cellgro, cat.no.15-041-CV), followed by incubation with human peripheral blood mononuclear cells (PBMC, generated by Ficoll from fresh human blood) at 37° C. for 24 h, to obtain the cultured PBMC.
2. The cultured PBMC were stimulated with different agonist as followed:
(1) the cultured PBMC were stimulated using 1 μM CpGA (Invivogen, cat.no. tlrl-2216), so that the plasmacytoid dendritic cells (pDC, the major type-I interferon producing cells in vivo) contained therein can produce type I interferon.
(2) the cultured PBMC were stimulated using 1 μg/mL R848 (Invivogen, cat.no. tlrl-r848), so that the plasmacytoid dendritic cells (pDC, the major type-I interferon producing cells in vivo) contained therein can produce type I interferon.
(3) the cultured PBMC were directly stimulated using 500 μg/ml IFNα2b (Cedarlane, cat.no. CL 106-04E-100UG).
3. 14 hours after the stimulation, the stimulated cells were harvested. RNA were extracted to prepare cDNA by reverse transcription.
4. Using the fluorescence real-time PCR to detect the RNA level of IFN effector genes Mx2 and ISGI5 in each of the stimulated cell PBMC, in which GAPDH was used as an internal control gene.

```
The primer sequences of Mx2 were:
Mx2-F:
CAGAGGCAGCGGAATCGTAA,       (SEQ ID NO: 41)

Mx2-R:
TGAAGCTCTAGCTCGGTGTTC,      (SEQ ID NO: 42)

The primer sequences of ISG15 were:
ISG15-F:
CCCACAGCCCACAGCCAT,         (SEQ ID NO: 43)

ISG15-R:
TTCTGGGTGATCTGCGCCTT,       (SEQ ID NO: 44)

The primer sequences of GAPDH were:
GAPDH-F:
AGCCACATCGCTCAGACAC,        (SEQ ID NO: 45)

GAPDH-R:
GCCCAATACGACCAAATCC.        (SEQ ID NO: 46)
```

Figure 14:
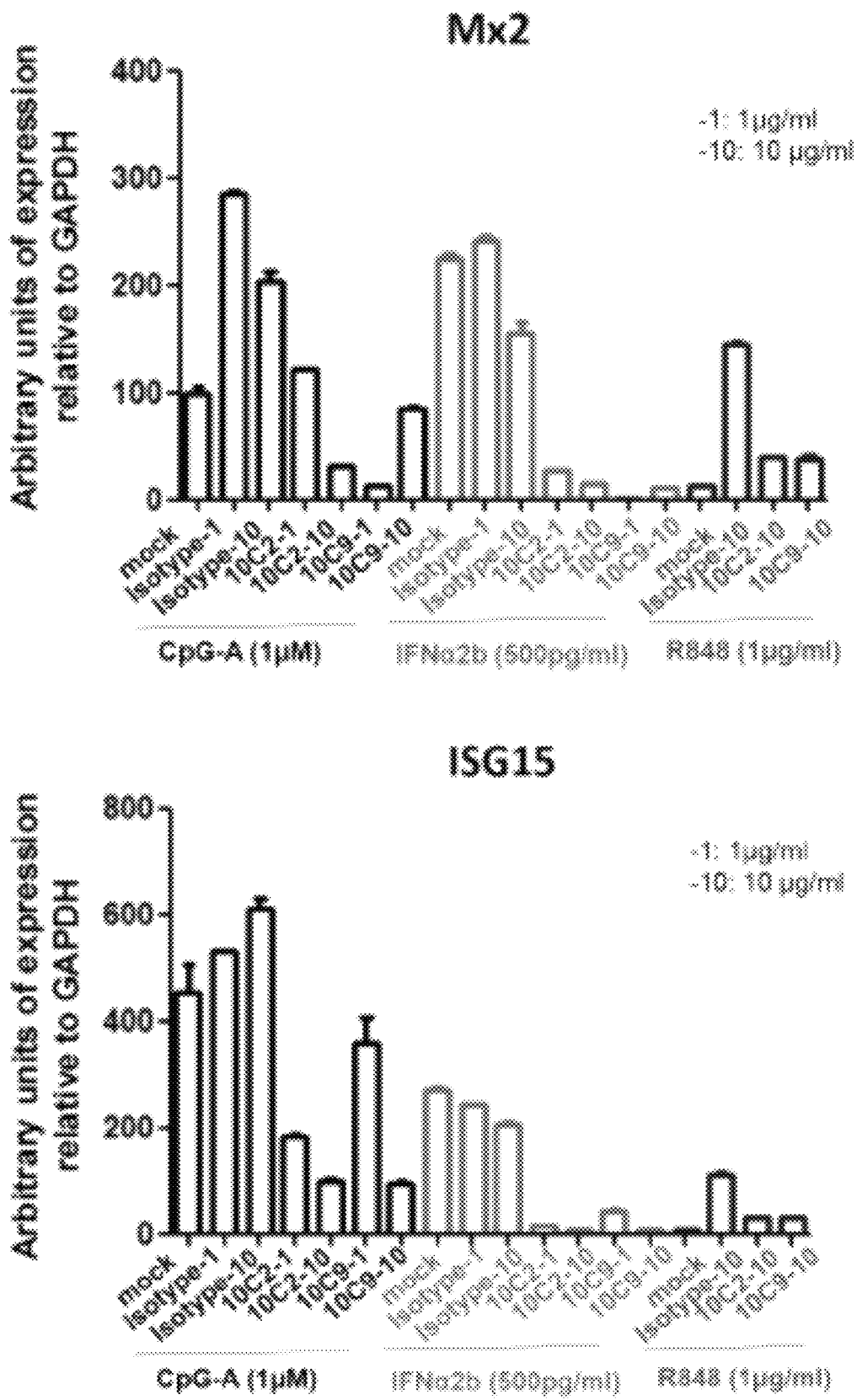
FIG. 14 shows that IFNAR1 monoclonal antibodies10C2 and 10C9 inhibit the biological activity of type I interferon on human peripheral blood monocyte cells stimulated with stimulant.

The results are shown in FIG. 14. "mock" represents istotype RPMI medium control, "Isotype" represents isotype control of the antibodies (mIgG2a, Biolegend). As shown in the figures, after addition of IFNAR1 monoclonal antibody 10C2 and 10C9, the RNA expression levels of the type I interferon effector genes Mx2 and ISGI5 in the stimulated cells decreased significantly. This indicated that the IFNAR1 monoclonal antibodies 10C2 and 10C9 both can effectively block the stimulation signals induced by endogenous type I interferon and external type I interferon.

INDUSTRIAL APPLICATIONS

The antibodies (and the immuno-conjugates and the bispecific molecules thereof) of the present disclosure can be used to detect the level of IFNAR1 or the level of IFNAR1-expressing cells, or to detect the presence of IFNAR1 in samples, or to determine the amount of IFNAR1. In another aspect, the antibodies (and the immuno-conjugates and the bispecific molecules thereof) of the present disclosure further has diagnostic and therapeutic applications in vitro and in vivo, including administering the anti-IFNAR1 antibodies or its antigen-binding portions thereof (and the immuno-conjugates and the bispecific molecules thereof) of the present disclosure, or in combination with an additional agent, to treat, prevent or diagnose a variety of type I interferon-mediated diseases. For example, the antibodies of the present disclosure can be used to treat type I interferon-mediated diseases such as inflammatory bowel disease (including ulcerative colitis and Crohn's disease), autoimmune thyroid disease (including autoimmune primary hypothyroidism, Graves' disease. Hashimoto's thyroiditis and destructive thyroiditis with hypothyroidism). RA, psoriasis and psoriatic arthritis, HIV infection or AIDS, by administering to a subject in need thereof. The antibodies of the present disclosure can also be used in a transplant recipient, to inhibit allograft rejection and/or prolong the survival of the allograft.

What is claimed is:

1. An anti-IFNAR1 monoclonal antibody or antigen-binding portion thereof, comprising
a heavy chain CDR1 (HCDR1) having an amino acid sequence of SEQ ID NO:3 or SEQ ID NO:13, a HCDR2 having an amino acid sequence of SEQ ID NO:4 or SEQ ID NO:14, and a HCDR3 having an amino acid sequence of SEQ ID NO:5 or SEQ ID NO:15; and
a light chain CDR1 (LCDR1) having an amino acid sequence of SEQ ID NO:8 or SEQ ID NO:18, a LCDR2 having an amino acid sequence of SEQ ID NO:9 or SEQ ID NO:19 and a LCDR3 having an amino acid sequence of SEQ ID NO:10 or SEQ ID NO:20,
wherein the antibody or antigen-binding portion thereof binds to all or part of SD2 domain and all or part of SD3 domain, and inhibits the biological activity of Type I interferons.

2. The antibody or antigen-binding portion thereof of claim 1, wherein:
the heavy chain variable region of the antibody or antigen-binding portion thereof, comprising sequentially the protein encoded by mouse IGHV9-3 gene, the protein encoded by mouse IGHD2-13 gene, the protein encoded by mouse IGHJ1 gene; and the light chain variable region of the antibody or antigen-binding portion thereof, comprising sequentially the protein encoded by mouse IGHV6-13gene, the protein encoded by mouse IGHJ5 gene; or
the heavy chain variable region of the antibody or antigen-binding portion thereof, comprising sequentially the protein encoded by mouse IGHV9-3 gene, the protein encoded by mouse IGHD1-1 gene, the protein encoded by mouse TGHJ3 gene, and the light chain variable region of the antibody or antigen-binding portion comprising the protein encoded by mouse IGHV6-15 gene, and the protein encoded by mouse TGHJ2 gene.

3. The anti-IFNAR1 monoclonal antibody or antigen-binding portion thereof of claim 1, comprising:
a HCDR1 having an amino acid sequence of SEQ ID NO: 3, a HCDR2 having an amino acid sequence of SEQ ID NO: 4 and a HCDR3 having an amino acid sequence of SEQ ID NO: 5; and a LCDR1 having an amino acid sequence of SEQ ID NO: 8, a LCDR2 having an amino acid sequence of SEO ID NO: 9 and a LCDR3 having an amino acid sequence of SEQ ID NO: 10; or
a HCDR1 having an amino acid sequence of SEQ ID NO: 13, a HCDR2 having an amino acid sequence of SEQ ID NO: 14 and a HCDR3 having an amino acid sequence of SEQ ID NO: 15; and a LCDR1 having an amino acid sequence of SEO ID NO: 18, a LCDR2 having an amino acid sequence of SEQ ID NO: 19 and a LCDR3 having an amino acid sequence of SEQ ID NO: 20.

4. The anti-IFNAR1 monoclonal antibody or antigen-binding portion thereof of claim 1, comprising:
a heavy chain variable region having an amino acid sequence of SEQ ID NO: 2 and a light chain variable region having an amino acid sequence of SEQ ID NO: 7, or a heavy chain variable region having an amino acid sequence of SEQ ID NO: 12 and a light chain variable region having an amino acid sequence of SEQ ID NO: 17.

5. The anti-IFNAR1 monoclonal antibody or antigen-binding portion thereof of claim 1, comprising:
   a heavy chain variable region encoded by a nucleotide sequence of SEQ ID NO: 1 and a light chain variable region encoded by a nucleotide sequence of SEO ID NO:6; or
   a heavy chain variable region encoded by a nucleotide sequence of SEQ ID NO: 11 and a light chain variable region encoded by a nucleotide sequence of SEO ID NO:16.

6. A type I interferon antagonist, comprising the anti-IFNAR1 antibody or antigen-binding portion thereof of claim 1.

7. A composition comprising the anti-IFNAR1 antibody, or antigen-binding portion thereof of claim 1.

8. An immunoconjugate comprising the anti-IFNAR1 antibody, or antigen-binding portion thereof of claim 1.

9. The immunoconjugate of claim 8, further comprises a pharmaceutically acceptable carrier.

10. A humanized antibody derived from humanization of the antibody, antigen-binding portion thereof of claim 1.

11. A bispecific molecule comprising the specific binding site of the antibody, or antigen-binding portion thereof of claim 1.

12. A biomaterial related to the antibody, or antigen-binding portion thereof of claim 1, which is any one of A1)-A12):
   A1) the nucleic acid molecule encoding the antibody, or antigen-binding portion thereof of claim 1;
   A3) an expression vector comprising the nucleic acid molecule of A1);
   A5) a recombinant cell comprising the nucleic acid molecule of A1);
   A7) a recombinant cell comprising the expression vector of A3);
   A9) a transgenic cell line comprising the nucleic acid molecule of A1); and
   A11) a transgenic cell line comprising the expression vector of A3).

13. A method for inhibiting biological activity of a type I interferon on a cell expressing interferon alpha receptor 1, comprising contacting the cell expressing IFNAR1 with the antibody or antigen binding portion thereof of claim 1.

14. A method of treating a type-I interferon-mediated disease or disorder in a subject in need of treatment comprising administering to the subject the antibody, or antigen-binding portion thereof, of claim 1, such that the type-I interferon mediated disease in the subject is treated, wherein the type-I interferon-mediated disease or disorder is an interferon aloha-mediated disease or disorder selected from the group consisting of systemic lupus erythematosus, insulin dependent diabetes mellitus, inflammatory bowel disease, multipole sclerosis, psoriasis, autoimmune thyroiditis, rheumatoid arthritis and glomerulonephritis.

15. A method for inhibiting the biological activity of type I interferons in type I interferons signaling reporter cells, comprising incubating the antibody or antigen binding portion thereof of claim 1 with the type I interferons signaling reporter cells.

16. A method for inhibiting the biological activity of type I interferons in agonists stimulated human peripheral blood mononuclear cells, comprising incubating the antibody or antigen binding portion thereof of claim 1 with the agonists stimulated human peripheral blood mononuclear cells.

17. A method for preparing an anti-IFNAR1 antibody, comprising:
   1) providing:
      (i) a sequence of the heavy chain variable region of the anti-IFNAR1 antibody, comprising CDR1 sequence selected from SEQ ID NO:3 and SEQ ID NO:13, CDR2 sequence selected from SEQ ID NO:4 and SEQ ID NO:14, and CDR3 sequence selected from SEQ ID NO:5 and SEQ ID NO:15; or
      (ii) a sequence of the light chain variable region of the anti-IFNAR1 antibody, comprising CDR1 sequence selected from SEQ ID NO:8 and SEQ ID NO:18, CDR2 sequence selected from SEQ ID NO:9 and SEQ ID NO:19, and CDR3 sequence selected from SEQ ID NO:10 and SEQ ID NO:20;
   2) expressing the anti-IFNAR1 antibody.

18. A hybridoma cell having a deposit number of CGMCC deposit No: 12542 or CGMCC deposit No: 12543.

19. A method for treating type I interferon-mediated disease or diseases caused by type I interferons abnormality in a subject, comprising administering to the subject the antibody or antigen binding portion thereof produced by the hybridoma cells of claim 18, such that the type-I interferon-mediated disease or diseases caused by type I interferons abnormality in the subject is treated, wherein the type-I interferon-mediated disease is an interferon aloha-mediated disease, and wherein the disease or disorder is selected from the group consisting of systemic lupus erythematosus, insulin dependent diabetes mellitus, inflammatory bowel disease, multiple sclerosis, psoriasis, autoimmune thyroiditis, rheumatoid arthritis and glomerulonephritis.

20. A method for inhibiting the biological activity of type I interferons in type I interferons signaling reporter cells, comprising incubating the antibody or antigen binding portion thereof produced by the hybridoma cells of claim 18 the type I interferons signaling reporter cells.

21. A method for inhibiting the biological activity of type I interferons in agonists stimulated human peripheral blood mononuclear cells, comprising incubating the antibody or antigen binding portion thereof produced by the hybridoma cells of claim 18 with the agonists stimulated human peripheral blood mononuclear cells.

* * * * *

SEQUENCE LISTING

<160> NUMBER OF SEQ ID NOS: 56

<210> SEQ ID NO 1
<211> LENGTH: 369
<212> TYPE: DNA
<213> ORGANISM: Artificial Sequence
<220> FEATURE:
<223> OTHER INFORMATION: Synthetic

<400> SEQUENCE: 1

```
cagatccagt tggtgcagtc tggacctgag ctgaagaagc ctggagagac agtcaagatc      60
tcctgcaagg cttctgggta taccttcaca aactatggaa tgaactgggt gaagcaggct    120
ccaggaaagg gtttaaagtg gatgggctgg ataaacacct acactggaga accaacatat    180
tctgatgact tcaagggacg gtttgccttc tctttggaga cctctgccag cactgccaat    240
ttgcagatca acaacctcaa agatgaggac gcggctacat acttctgtgc aagagagggg    300
gctatctact atggtgacta cgtgtacttc ggtgtctggg gcgcagggac cacggtcacc    360
gtctcctca                                                            369
```

<210> SEQ ID NO 2
<211> LENGTH: 123
<212> TYPE: PRT
<213> ORGANISM: Artificial Sequence
<220> FEATURE:
<223> OTHER INFORMATION: Synthetic

<400> SEQUENCE: 2

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asn Tyr
            20                  25                  30
Gly Met Asn Trp Val Lys Gln Ala Pro Gly Lys Gly Leu Lys Trp Met
        35                  40                  45
Gly Trp Ile Asn Thr Tyr Thr Gly Glu Pro Thr Tyr Ser Asp Asp Phe
    50                  55                  60
Lys Gly Arg Phe Ala Phe Ser Leu Glu Thr Ser Ala Ser Thr Ala Asn
65                  70                  75                  80
Leu Gln Ile Asn Asn Leu Lys Asp Glu Asp Ala Ala Thr Tyr Phe Cys
                85                  90                  95
Ala Arg Glu Gly Ala Ile Tyr Tyr Gly Asp Tyr Val Tyr Phe Gly Val
            100                 105                 110
Trp Gly Ala Gly Thr Thr Val Thr Val Ser Ser
        115                 120
```

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

```
Gly Tyr Thr Phe Thr Asn Tyr Gly
1               5
```

<210> SEQ ID NO 4
<211> LENGTH: 8
<212> TYPE: PRT
<213> ORGANISM: Artificial Sequence
<220> FEATURE:

```
<223> OTHER INFORMATION: Synthetic

<400> SEQUENCE: 4

Ile Asn Thr Tyr Thr Gly Glu Pro
1               5

<210> SEQ ID NO 5
<211> LENGTH: 16
<212> TYPE: PRT
<213> ORGANISM: Artificial Sequence
<220> FEATURE:
<223> OTHER INFORMATION: Synthetic

<400> SEQUENCE: 5

Ala Arg Glu Gly Ala Ile Tyr Tyr Gly Asp Tyr Val Tyr Phe Gly Val
1               5                   10                  15

<210> SEQ ID NO 6
<211> LENGTH: 324
<212> TYPE: DNA
<213> ORGANISM: Artificial Sequence
<220> FEATURE:
<223> OTHER INFORMATION: Synthetic

<400> SEQUENCE: 6
gacattgtga tgacccagtc tcaaaaattc atgtccacat cagtaggaga cagggtcagc        60
atcacctgca aggccagtca gaatgtgggt actgctgtag cctggtatca agagaaacca       120
ggacaatctc ctaaactact gatttactcg gcatccaatc gatacactgg agtccctgat       180
cgcttcacag gcagtggatc tgggacagct ttcactctca ccatcagcaa tatgcagtct       240
gaagacctgg cagattattt ctgccagcaa tattacaatt atcctctcac gttcggtgct       300
gggaccaagc tggaggtgaa acgg                                              324

<210> SEQ ID NO 7
<211> LENGTH: 108
<212> TYPE: PRT
<213> ORGANISM: Artificial Sequence
<220> FEATURE:
<223> OTHER INFORMATION: Synthetic

<400> SEQUENCE: 7

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
                20                  25                  30

Val Ala Trp Tyr Gln Glu Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Ala Phe Thr Leu Thr Ile Ser Asn Met Gln Ser
65                  70                  75                  80

Glu Asp Leu Ala Asp Tyr Phe Cys Gln Gln Tyr Tyr Asn Tyr Pro Leu
                85                  90                  95

Thr Phe Gly Ala Gly Thr Lys Leu Glu Val Lys Arg
            100                 105

<210> SEQ ID NO 8
<211> LENGTH: 6
<212> TYPE: PRT
<213> ORGANISM: Artificial Sequence
<220> FEATURE:
```

```
<223> OTHER INFORMATION: Synthetic

<400> SEQUENCE: 8

Gln Asn Val Gly Thr Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Ser Ala Ser Asn Arg Tyr
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic

<400> SEQUENCE: 10

Gln Gln Tyr Tyr Asn Tyr
1               5

<210> SEQ ID NO 11
<211> LENGTH: 369
<212> TYPE: DNA
<213> ORGANISM: Artificial sequence
<220> FEATURE:
<223> OTHER INFORMATION: Synthetic

<400> SEQUENCE: 11
cagatccagt tggtgcagtc tggacctgag ctgaagaagc ctggagagac agtcaagatc      60
tcctgcaagg cttctggata taccttcaca aactatggag tgaactggat gaagcaggct     120
ccaggaaagg gtttaaagtg gatgggctgg ataaacacct acactggaga gccaacatat     180
gctgatgact caagggacg ctttgccttc tctttggaaa cctctgccag cactgcctat      240
ttacagatca caaacctcaa aaatgaggac acggctacat atttctgtgc aagagagggg     300
gtttattact acggtgattg ggcctggctt gcttactggg gccaaggac cctggtcact      360 gtctctgca                                                             369

<210> SEQ ID NO 12
<211> LENGTH: 123
<212> TYPE: PRT
<213> ORGANISM: Artificial sequence
<220> FEATURE:
<223> OTHER INFORMATION: Synthetic

<400> SEQUENCE: 12

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Val Asn Trp Met Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60
```

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Glu Gly Val Tyr Tyr Tyr Gly Asp Trp Ala Trp Leu Ala Tyr
            100                 105                 110

Trp Gly Gln Gly Thr Leu Val Thr Val Ser Ala
        115                 120
```

<210> SEQ ID NO 13
<211> LENGTH: 8
<212> TYPE: PRT
<213> ORGANISM: Artificial sequence
<220> FEATURE:
<223> OTHER INFORMATION: Synthetic

<400> SEQUENCE: 13

```
Gly Tyr Thr Phe Thr Asn Tyr Gly
 1               5
```

<210> SEQ ID NO 14
<211> LENGTH: 8
<212> TYPE: PRT
<213> ORGANISM: Artificial sequence
<220> FEATURE:
<223> OTHER INFORMATION: Synthetic

<400> SEQUENCE: 14

```
Ile Asn Thr Tyr Thr Gly Glu Pro
 1               5
```

<210> SEQ ID NO 15
<211> LENGTH: 16
<212> TYPE: PRT
<213> ORGANISM: Artificial sequence
<220> FEATURE:
<223> OTHER INFORMATION: Synthetic

<400> SEQUENCE: 15

```
Ala Arg Glu Gly Val Tyr Tyr Tyr Gly Asp Trp Ala Trp Leu Ala Tyr
 1               5                  10                  15
```

<210> SEQ ID NO 16
<211> LENGTH: 321
<212> TYPE: DNA
<213> ORGANISM: Artificial sequence
<220> FEATURE:
<223> OTHER INFORMATION: Synthetic

<400> SEQUENCE: 16

```
gacattgtga tgacccagtc tcaaaaattc atttccacat cagtaggaga cagggtcagc     60
gtcacctgca aggccagtca gaatgtgggt actaatgtag cctggtatca acagaaacca    120
ggtcaatctc ctaaaacact gatttactcg acatcctacc ggtacaatgg agtccctgat    180
cgcttcacag gcagtggatc tgggacagat ttcactctca ccatcagcaa tgtgcagtct    240
gaagacttgg cagagtattt ctgtcagcaa tataacagct attacacgtt cggagggggg    300
accaagctgg aaataaaacg g                                              321
```

<210> SEQ ID NO 17
<211> LENGTH: 106
<212> TYPE: PRT
<213> ORGANISM: Artificial sequence
<220> FEATURE:

<223> OTHER INFORMATION: Synthetic

<400> SEQUENCE: 17

```
Asp Ile Val Met Thr Gln Ser Gln Lys Phe Ile Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Thr Leu Ile
        35                  40                  45

Tyr Ser Thr Ser Tyr Arg Tyr Asn Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Tyr Thr
                85                  90                  95

Phe Gly Gly Gly Thr Lys Leu Glu Ile Lys
            100                 105
```

<210> SEQ ID NO 18
<211> LENGTH: 6
<212> TYPE: PRT
<213> ORGANISM: Artificial sequence
<220> FEATURE:
<223> OTHER INFORMATION: Synthetic

<400> SEQUENCE: 18

```
Gln Asn Val Gly Thr Asn
1               5
```

<210> SEQ ID NO 19
<211> LENGTH: 6
<212> TYPE: PRT
<213> ORGANISM: Artificial sequence
<220> FEATURE:
<223> OTHER INFORMATION: Synthetic

<400> SEQUENCE: 19

```
Ser Ala Ser Asn Arg Tyr
1               5
```

<210> SEQ ID NO 20
<211> LENGTH: 8
<212> TYPE: PRT
<213> ORGANISM: Artificial sequence
<220> FEATURE:
<223> OTHER INFORMATION: Synthetic

<400> SEQUENCE: 20

```
Gln Gln Tyr Asn Ser Tyr Tyr Thr
1               5
```

<210> SEQ ID NO 21
<211> LENGTH: 123
<212> TYPE: PRT
<213> ORGANISM: Artificial sequence
<220> FEATURE:
<223> OTHER INFORMATION: Synthetic

<400> SEQUENCE: 21

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30
```

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Gly Ala Ile Tyr Tyr Gly Asp Tyr Val Tyr Phe Gly Val
                100                 105                 110

Trp Gly Ala Gly Thr Thr Val Thr Val Ser Ser
            115                 120

<210> SEQ ID NO 22
<211> LENGTH: 107
<212> TYPE: PRT
<213> ORGANISM: Artificial sequence
<220> FEATURE:
<223> OTHER INFORMATION: Synthetic

<400> SEQUENCE: 22

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Val Lys
                100                 105

<210> SEQ ID NO 23
<211> LENGTH: 123
<212> TYPE: PRT
<213> ORGANISM: Artificial sequence
<220> FEATURE:
<223> OTHER INFORMATION: Synthetic

<400> SEQUENCE: 23

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Gly Val Tyr Tyr Tyr Gly Asp Trp Ala Trp Leu Ala Tyr

```
                    100                 105                 110

Trp Gly Gln Gly Thr Leu Val Thr Val Ser Ala
            115                 120

<210> SEQ ID NO 24
<211> LENGTH: 106
<212> TYPE: PRT
<213> ORGANISM: Artificial sequence
<220> FEATURE:
<223> OTHER INFORMATION: Synthetic

<400> SEQUENCE: 24

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Tyr Thr
                85                  90                  95

Phe Gly Gly Gly Thr Lys Leu Glu Ile Lys
            100                 105

<210> SEQ ID NO 25
<211> LENGTH: 34
<212> TYPE: DNA
<213> ORGANISM: Artificial Sequence
<220> FEATURE:
<223> OTHER INFORMATION: Synthetic

<400> SEQUENCE: 25
ctagctagca agtctaaggg ctctgaggac agac                               34

<210> SEQ ID NO 26
<211> LENGTH: 34
<212> TYPE: DNA
<213> ORGANISM: Artificial Sequence
<220> FEATURE:
<223> OTHER INFORMATION: Synthetic

<400> SEQUENCE: 26
cccaagcttc aaatgccctg ctgtacttac cagt                               34

<210> SEQ ID NO 27
<211> LENGTH: 42
<212> TYPE: DNA
<213> ORGANISM: Artificial Sequence
<220> FEATURE:
<223> OTHER INFORMATION: Synthetic

<400> SEQUENCE: 27
ctagctagct ctagagccac catgatggtc gtcctcctgg gc                      42

<210> SEQ ID NO 28
<211> LENGTH: 46
<212> TYPE: DNA
<213> ORGANISM: Artificial Sequence
<220> FEATURE:
<223> OTHER INFORMATION: Synthetic
```

```
<400> SEQUENCE: 28
gggtccggaa cctcctcctc ccacagcata aatgacaaac gggaga            46

<210> SEQ ID NO 29
<211> LENGTH: 42
<212> TYPE: DNA
<213> ORGANISM: Artificial Sequence
<220> FEATURE:
<223> OTHER INFORMATION: Synthetic

<400> SEQUENCE: 29
ctagctagct ctagagccac catgatggtc gtcctcctgg gc                42

<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
cttgaccagg catcctagag tca                                     23

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
gayattgtgm tsacmcarwc tmca                                    24

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
ggatacagtt ggtgcagcat c                                       21

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
attgacgcaa atgggcggta                                         20

<210> SEQ ID NO 34
<211> LENGTH: 45
<212> TYPE: DNA
<213> ORGANISM: Artificial Sequence
<220> FEATURE:
<223> OTHER INFORMATION: Synthetic

<400> SEQUENCE: 34
caggtggaaa aaatctaaaa cagattggtc ctccagaagt acatt             45

<210> SEQ ID NO 35
```

<210> SEQ ID NO 35
<211> LENGTH: 44
<212> TYPE: DNA
<213> ORGANISM: Artificial Sequence
<220> FEATURE:
<223> OTHER INFORMATION: Synthetic

<400> SEQUENCE: 35
acttctggag gaccaatctg ttttagattt ttccacctg cggc  44

<210> SEQ ID NO 36
<211> LENGTH: 44
<212> TYPE: DNA
<213> ORGANISM: Artificial Sequence
<220> FEATURE:
<223> OTHER INFORMATION: Synthetic

<400> SEQUENCE: 36
ttacaccatt tcgcaaagct gaactacctc caccagaaaa tata  44

<210> SEQ ID NO 37
<211> LENGTH: 45
<212> TYPE: DNA
<213> ORGANISM: Artificial Sequence
<220> FEATURE:
<223> OTHER INFORMATION: Synthetic

<400> SEQUENCE: 37
ttttctggtg gaggtagttc agctttgcga aatggtgtaa atgag  45

<210> SEQ ID NO 38
<211> LENGTH: 45
<212> TYPE: DNA
<213> ORGANISM: Artificial Sequence
<220> FEATURE:
<223> OTHER INFORMATION: Synthetic

<400> SEQUENCE: 38
cagttgaaaa tgaactacct ttcctacttc ctccagtctt taaca  45

<210> SEQ ID NO 39
<211> LENGTH: 45
<212> TYPE: DNA
<213> ORGANISM: Artificial Sequence
<220> FEATURE:
<223> OTHER INFORMATION: Synthetic

<400> SEQUENCE: 39
actggaggaa gtaggaaagc aggtagttca ttttcaactg tggtc  45

<210> SEQ ID NO 40
<211> LENGTH: 46
<212> TYPE: DNA
<213> ORGANISM: Artificial Sequence
<220> FEATURE:
<223> OTHER INFORMATION: Synthetic

<400> SEQUENCE: 40
gggtccggaa cctcctcctc ccacagcata aatgacaaac gggaga  46

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
cagaggcagc ggaatcgtaa                                           20

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
tgaagctcta gctcggtgtt c                                         21

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cccacagccc acagccat                                             18

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ttctgggtga tctgcgcctt                                           20

<210> SEQ ID NO 45
<211> LENGTH: 19
<212> TYPE: DNA
<213> ORGANISM: Artificial Sequence
<220> FEATURE:
<223> OTHER INFORMATION: Synthetic

<400> SEQUENCE: 45
agccacatcg ctcagacac                                            19

<210> SEQ ID NO 46
<211> LENGTH: 19
<212> TYPE: DNA
<213> ORGANISM: Artificial Sequence
<220> FEATURE:
<223> OTHER INFORMATION: Synthetic

<400> SEQUENCE: 46
gcccaatacg accaaatcc                                            19

<210> SEQ ID NO 47
<211> LENGTH: 19
<212> TYPE: PRT
<213> ORGANISM: Artificial Sequence
<220> FEATURE:
<223> OTHER INFORMATION: Synthetic

<400> SEQUENCE: 47

Met Ala Trp Val Trp Thr Leu Leu Phe Leu Met Ala Ala Ala Gln Ser
1               5                   10                  15

Ala Gln Ala

-continued

<210> SEQ ID NO 48
<211> LENGTH: 24
<212> TYPE: PRT
<213> ORGANISM: Artificial Sequence
<220> FEATURE:
<223> OTHER INFORMATION: Synthetic

<400> SEQUENCE: 48

Met Gly Phe Lys Met Glu Ser His Thr Gln Ala Phe Val Phe Ala Phe
1               5                   10                  15

Leu Trp Leu Ser Gly Val Asp Gly
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic

<400> SEQUENCE: 49

Met Glu Ser Gln Thr Gln Val Phe Val Tyr Met Leu Leu Trp Leu Ser
1               5                   10                  15

Gly Val Asp Gly
            20

<210> SEQ ID NO 50
<211> LENGTH: 103
<212> TYPE: PRT
<213> ORGANISM: Artificial Sequence
<220> FEATURE:
<223> OTHER INFORMATION: Synthetic

<400> SEQUENCE: 50

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Lys Pro Gly Gln Ser Pro Lys Leu Leu Ile Tyr
        35                  40                  45

Ser Ala Ser Asn Arg Tyr Thr Gly Val Pro Asp Arg Phe Thr Gly Ser
    50                  55                  60

Gly Ser Gly Thr Phe Thr Leu Thr Ile Ser Asn Met Gln Ser Glu Asp
65                  70                  75                  80

Leu Ala Asp Tyr Phe Cys Gln Gln Tyr Tyr Pro Leu Thr Phe Gly Ala
                85                  90                  95

Gly Thr Lys Leu Glu Val Lys
            100

<210> SEQ ID NO 51
<211> LENGTH: 123
<212> TYPE: PRT
<213> ORGANISM: Artificial Sequence
<220> FEATURE:
<223> OTHER INFORMATION: Synthetic

<400> SEQUENCE: 51

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Met Lys Gln Ala Pro Gly Lys Gly Leu Lys Trp Met

```
            35                  40                  45
Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                85                  90                  95

Ala Arg Glu Gly Val Tyr Tyr Gly Asp Trp Ala Trp Leu Ala Tyr
                100                 105                 110

Trp Gly Gln Gly Thr Leu Val Thr Val Ser Ala
            115                 120
```

```
<210> SEQ ID NO 52
<211> LENGTH: 103
<212> TYPE: PRT
<213> ORGANISM: Artificial Sequence
<220> FEATURE:
<223> OTHER INFORMATION: Synthetic

<400> SEQUENCE: 52

Asp Ile Val Met Thr Gln Ser Gln Lys Phe Ile Ser Thr Ser Val Gly
 1               5                  10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Leu Ile Tyr
            35                  40                  45

Ser Ser Tyr Arg Tyr Gly Val Pro Asp Arg Phe Thr Gly Ser Gly Ser
        50                  55                  60

Gly Thr Asp Phe Thr Leu Thr Ile Ser Asn Val Gln Ser Glu Asp Leu
 65                  70                  75                  80

Ala Glu Tyr Phe Cys Gln Gln Tyr Asn Ser Tyr Tyr Thr Phe Gly Gly
                85                  90                  95

Gly Thr Lys Leu Glu Ile Lys
                100
```

```
<210> SEQ ID NO 53
<211> LENGTH: 120
<212> TYPE: PRT
<213> ORGANISM: Artificial Sequence
<220> FEATURE:
<223> OTHER INFORMATION: Synthetic

<400> SEQUENCE: 53

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Leu
 65                  70                  75                  80

Gln Ile Asn Asn Leu Lys Glu Asp Ala Thr Tyr Phe Cys Ala Arg Glu
                85                  90                  95

Gly Ala Ile Tyr Tyr Gly Asp Tyr Val Tyr Phe Gly Val Trp Gly Ala
                100                 105                 110
```

Gly Thr Thr Val Thr Val Ser Ser
        115                 120

<210> SEQ ID NO 54
<211> LENGTH: 57
<212> TYPE: DNA
<213> ORGANISM: Artificial Sequence
<220> FEATURE:
<223> OTHER INFORMATION: Synthetic

<400> SEQUENCE: 54
atggcttggg tgtggacctt gctattcctg atggcagctg cccaaagtgc ccaagca            57

<210> SEQ ID NO 55
<211> LENGTH: 72
<212> TYPE: DNA
<213> ORGANISM: Artificial Sequence
<220> FEATURE:
<223> OTHER INFORMATION: Synthetic

<400> SEQUENCE: 55
atgggcttca agatggagtc tcatactcag gcctttgtat tcgcgtttct ctggttgtct            60
ggtgttgatg ga                                                              72

<210> SEQ ID NO 56
<211> LENGTH: 60
<212> TYPE: DNA
<213> ORGANISM: Artificial Sequence
<220> FEATURE:
<223> OTHER INFORMATION: Synthetic

<400> SEQUENCE: 56
atggagtcac agactcaggt ctttgtatac atgttgctgt ggttgtctgg tgttgatgga            60